United States Patent
Lorca et al.

(10) Patent No.: US 12,042,518 B2
(45) Date of Patent: Jul. 23, 2024

(54) LACTOBACILLUS SUPPLEMENT FOR PROMOTING GASTRIC AND IMMUNE HEALTH

(71) Applicant: UNIVERSITY OF FLORIDA RESEARCH FOUNDATION, INC., Gainesville, FL (US)

(72) Inventors: Graciela Liliana Lorca, Gainesville, FL (US); Claudio Gonzalez, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1102 days.

(21) Appl. No.: 16/470,802

(22) PCT Filed: Dec. 18, 2017

(86) PCT No.: PCT/US2017/067058
§ 371 (c)(1),
(2) Date: Jun. 18, 2019

(87) PCT Pub. No.: WO2018/112465
PCT Pub. Date: Jun. 21, 2018

(65) Prior Publication Data
US 2019/0336548 A1 Nov. 7, 2019

Related U.S. Application Data

(60) Provisional application No. 62/435,781, filed on Dec. 18, 2016.

(51) Int. Cl.
| | | |
|---|---|---|
| *A61K 35/747* | (2015.01) | |
| *A23L 33/135* | (2016.01) | |
| *A61K 9/00* | (2006.01) | |
| *A61K 9/50* | (2006.01) | |
| *A61P 1/14* | (2006.01) | |

(52) U.S. Cl.
CPC .......... *A61K 35/747* (2013.01); *A23L 33/135* (2016.08); *A61K 9/0056* (2013.01); *A61K 9/50* (2013.01); *A61P 1/14* (2018.01); *A23V 2002/00* (2013.01); *A23V 2400/151* (2023.08)

(58) Field of Classification Search
CPC ...... A61K 35/747; A61K 9/0056; A61K 9/50; A23L 33/135; A61P 1/14; A23V 2002/00; A23V 2400/151; A23Y 2220/43
See application file for complete search history.

(56) References Cited

U.S. PATENT DOCUMENTS

| | | | |
|---|---|---|---|
| 9,474,773 B2 * | 10/2016 | Neu | ............ A61P 1/14 |
| 2012/0315249 A1 | 12/2012 | Olmstead | |
| 2015/0196533 A1 | 7/2015 | Mao et al. | |

FOREIGN PATENT DOCUMENTS

| | | | | |
|---|---|---|---|---|
| WO | WO-2010079444 A1 * | 7/2010 | ............ | A23K 1/02 |
| WO | 2010096550 A2 | 8/2010 | | |

OTHER PUBLICATIONS

UKEssays. Gastric Acid Resistant Capsules Are Enteric Biology Essay. UKEssays. 2015;1-5.*
NINDS. Cephalic Disorders. NIH Publication No. 03-4339. 2003;1-24.*
Valladares et al. H2O2 production rate in Lactobacillus johnsonii is modulated via the interplay of a heterodimeric flavin oxidoreductase with a soluble 28 Kd. Front Microbiol. 2015;6(716):1-14.*
Gomes et al. Gut microbiota, probiotics and diabetes. Nutrition Journal. 2014;13(60):1-13.*
Diatribe. Type 1 Diabetes. https://diatribe.org/type-1-diabetes. 2014;1-5.*
EP17881458; Supplementary European Search Report; Jul. 24, 2020; 10 pages.
Del Piano Mario et al, "The use of probiotics in healthy volunteers with evacuation disorders and hard stool: a double-blind, randomized, placebo-controlled study", Journal of Clinical Gastroenterology, Sep. 2010, vol. 44, No. 1, pp. S30-S34.
Kaburagi et al., "Effect of Lactobacillus johnsonii La1 on immune function and serum albumin in aged and malnourished aged mice", Nutrition, Mar. 2007, vol. 23, No. 4, pp. 342-350.
Guillermo, E. Marcial et al., "Lactobacillus johnsonii N6.2 Modulated the Host Immune Responses: A Double-Blind randomized Trial in Healthy Adults", Frontiers in Immunology, Jun. 2017, vol. 8, No. 655, pp. 1-17.
Georgin-Lavialle, S. et al., "Decreased tryptophan and increased kynurenine levels in mastocytosis associated with digestive symptoms", Allergy, Mar. 2016, vol. 71, pp. 416-420.

(Continued)

*Primary Examiner* — Lynn Y Fan
(74) *Attorney, Agent, or Firm* — Timothy H. Van Dyke; WOLTER, VAN DYKE, DAVIS, PLLC

(57) ABSTRACT

The subject invention provides compositions for promoting good health. Specifically, the subject composition can be used for alleviating symptoms of indigestion, abdominal pain, and cephalic syndrome, including in healthy subjects. In preferred embodiments, the compositions comprise an effective amount of one or more *Lactobacillus* isolates. Preferably, the bacteria used as an active ingredient in the compositions of the subject invention are of the *L. johnsonii* N6.2 strain. The subject invention also provides methods for alleviating symptoms of indigestion, abdominal pain, and cephalic syndrome. These methods comprise the administration of a composition of the subject invention, wherein the composition preferably comprises an effective amount of one or more *Lactobacillus* isolates. Even more preferably, the subject method utilizes an effective amount of *L. johnsonii* N6.2.

11 Claims, 14 Drawing Sheets

(56) References Cited

OTHER PUBLICATIONS

Marcial, Guillermo E. et al., "Lactobacillus johnsonii N6.2 modulates the host immune responsesw: a double-blind, randomized trial in healthy adults", Frontiers in Immunology, Jun. 2017, vol. 8, article No. 655, p. 1-17.
Valladares, Ricardo et al., "Lactobacillus johnsonii inhibits indoleamine 2, 3-dioxygenase and alters tryptophan metabolite levels in BioBreeding rats", The FASEB Journal, Apr. 2013, vol. 27, pp. 1711-1720.
PCT/US2017/067058; PCT International Search Report and Written Opinion, Apr. 15, 2018, 12 pages.

\* cited by examiner

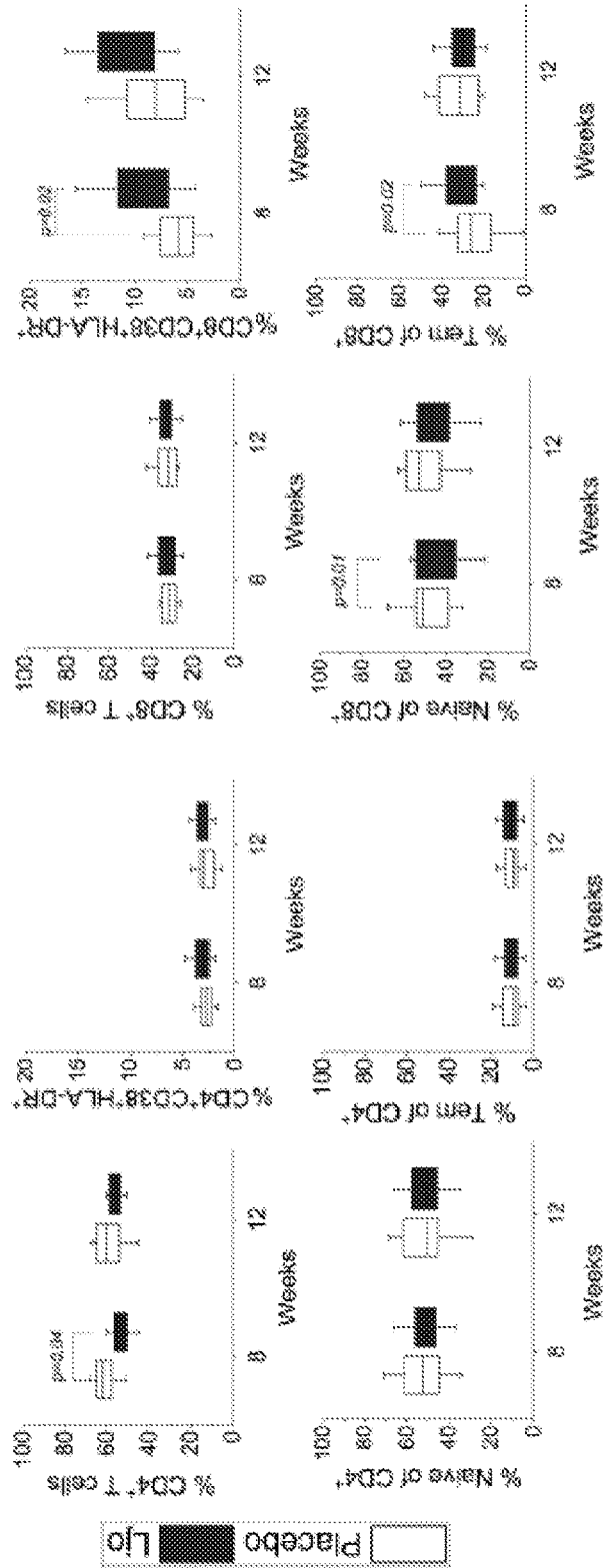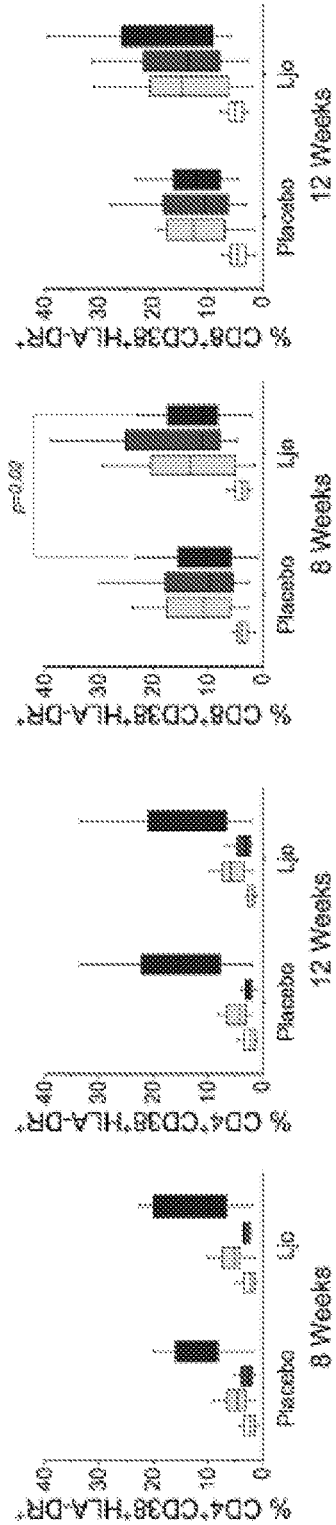
FIG. 8A
FIG. 8B
FIG. 8C

LACTOBACILLUS SUPPLEMENT FOR PROMOTING GASTRIC AND IMMUNE HEALTH

CROSS-REFERENCE TO A RELATED APPLICATION

This application claims the benefit of U.S. Provisional Patent Application Ser. No. 62/435,781, filed Dec. 18, 2016, which is incorporated herein by reference in its entirety.

STATEMENT REGARDING SPONSORED RESEARCH

This invention was made in part or whole with support under Grant No. I-INO-2014-176-A-V awarded by the Juvenile Diabetes Research Foundation.

BACKGROUND OF INVENTION

Commensal bacteria regulate a myriad of host processes and provide nutrients to their host, as well as their symbionts within the microbial community. In healthy individuals, these relationships are thought to occur in equilibrium. However, disruption of this equilibrium may contribute to a variety of conditions, including inflammatory bowel disease. In fact, recent studies have shown associations between gut microbiota and either the risk for or presence of an assortment of human diseases.

Probiotics are live microorganisms which, when administered in adequate amounts, confer a health benefit on the host. A number of *Lactobacillus* and *Bifidobacterium* species are Generally Regarded as Safe (GRAS) microorganisms and are widely used in dietary supplements as probiotics worldwide. However, the mechanisms by which these individual probiotics modulate host responses and immunity are diverse and are often strain-specific, rather than shared amongst genera.

In order to understand the role of the resident microbiota in T1D, a culture independent analysis of the bacteria in fecal samples collected from Biobreeding diabetes-resistant (BB-DR) and diabetes-prone (BB-DP) rats was performed. These experiments demonstrated a significant difference in *Lactobacillus* and *Bifidobacterium* species in the intestinal microbiota of DR and the DP rats which were correlated with health status (Roesch et al., 2009).

Given the observation of *L. johnsonii* N6.2 in protected DR rats, an intervention study using *L. johnsonii* N6.2 in BB-DP animals was performed. It was found that the administration of *L. johnsonii* N6.2 to BB-DP rats reduced the incidence of T1D. (Valladares et al., 2010).

In a recent publication from The Environmental Determinants of Diabetes in the Young (TEDDY) study group, there was a reported association between decreased risk of islet autoimmunity and early supplementation of probiotics (between the age of 0-27 days) when compared to no supplementation (Uusitalo et al., 2016).

BRIEF SUMMARY

The subject invention provides compositions for promoting good health. Specifically, the subject compositions can be used for alleviating symptoms of indigestion, abdominal pain, and cephalic syndrome in otherwise healthy subjects. In specific embodiments the subjects do not have and/or have not been diagnosed with diabetes, particularly, type 1 diabetes.

In preferred embodiments, the compositions comprise an effective amount of one or more *Lactobacillus* isolates. Preferably, the bacteria used as an active ingredient in the compositions of the subject invention are of the *L. johnsonii* N6.2 strain.

The subject invention also provides methods for alleviating symptoms of indigestion, abdominal pain, and cephalic syndrome. These methods comprise the administration of a composition of the subject invention, wherein the composition preferably comprises an effective amount of one or more *Lactobacillus* isolates. Even more preferably, the subject method utilizes an effective amount of *L. johnsonii* N6.2.

BRIEF DESCRIPTION OF THE FIGURES

FIGS. 8A-8C show T cell subset. 8A) Activated $CD4^+$ or 8B) $CD8^+$ T cells populations subsets [Naïve, Tem, activated (CD38+HLA-DR+)] were quantified after 8 or 12 weeks of treatment in the placebo and *L. johnsonii* N6.2 (Ljo) groups. Naïve (CCR7$^+$CD45RA$^+$), Tem (CCR7$^-$CD45RA$^-$), Tcm (CCR7$^+$CD45RA$^-$) and Temra (CCR7$^-$ CD45RA$^+$) were labeled with specific antibodies (8C). The concentration of cells shown has been normalized to the concentration found at T0 for each subject.

DETAILED DISCLOSURE

Figure 1:
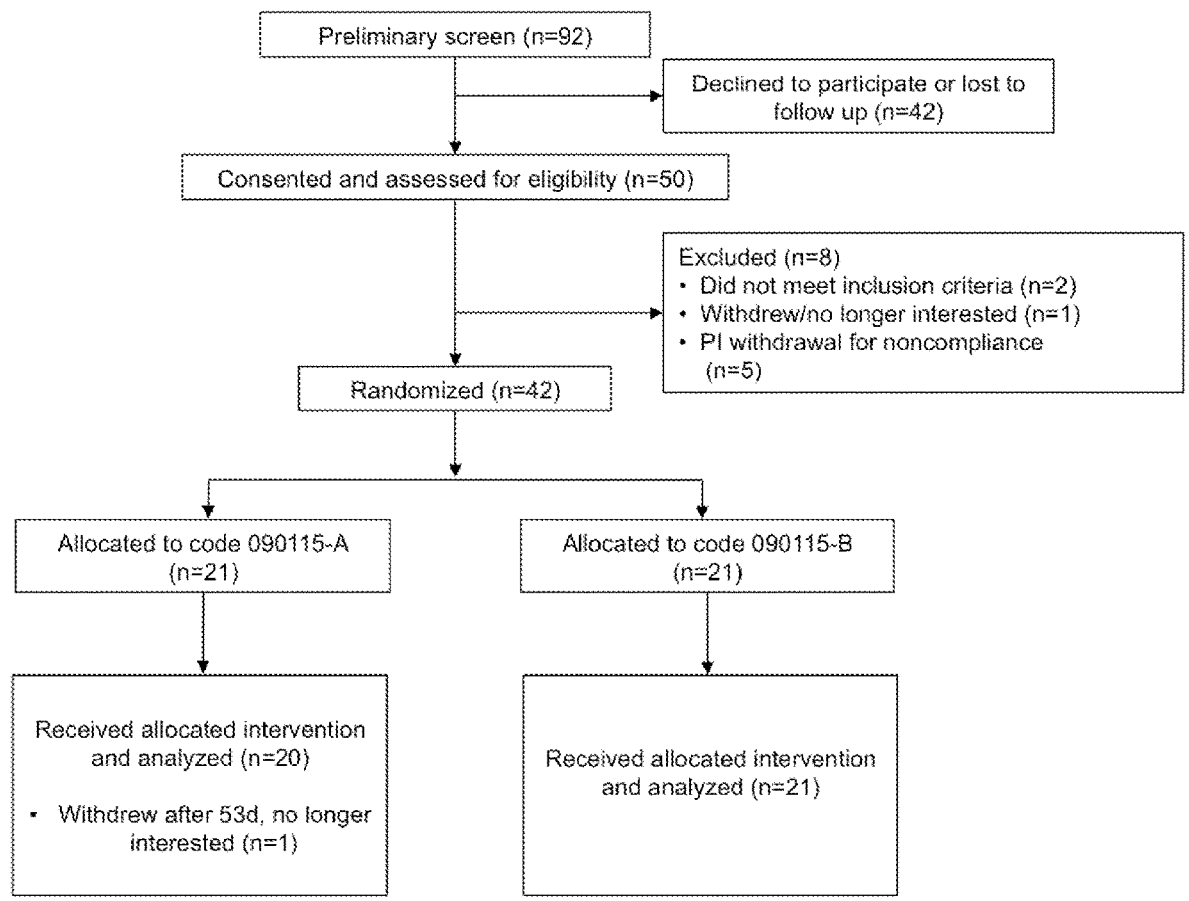
FIG. 1 shows a Study flow diagram to illustrate the number of subjects that were screened, consented and randomized. Code 090115-A was used for the placebo while Code 090115-B was used for *L. johnsonii* N6.2.

The subject invention provides compositions for promoting good health. Specifically, the subject composition can be used for alleviating symptoms of indigestion, abdominal pain, and cephalic syndrome, including in healthy subjects. In preferred embodiments, the compositions comprise an effective amount of one or more *Lactobacillus* isolates. Preferably, the bacteria used as an active ingredient in the compositions of the subject invention are of the *L. johnsonii* N6.2 strain.

The subject invention also provides methods for alleviating symptoms of indigestion, abdominal pain, and cephalic syndrome. These methods comprise the administration of a composition of the subject invention, wherein the composition preferably comprises an effective amount of one or more *Lactobacillus* isolates. Even more preferably, the subject method utilizes an effective amount of *L. johnsonii* N6.2.

A human trial was performed to evaluate the safety, tolerability, and general response to consumption of this microorganism in healthy individuals. The safety and tolerability of oral *L. johnnsonii* N6.2 was determined. It was found that *L. johnsonii* N6.2 preparation was well tolerated with no risks for healthy subjects. The hemogram and CMP data showed no significant differences between the probiotic and placebo groups throughout the treatment and after wash-out periods. No adverse events related to *L. johnsonii* N6.2 preparation were observed. *L. johnsonii* N6.2 survived intestinal transit, although no significant differences in the total numbers of LAB were observed among treatments. Results showed that *L. johnsonii* has the ability to survive and may colonize the intestinal tract without affecting the residing microbiota in healthy subjects.

Remarkably, significant changes on the kynurenine pathway metabolites as well as immune responses were observed in serum and peripheral blood while significant changes in certain GSRS syndromes were observed in the probiotic treatment group.

The GSRS has been used to evaluate gastrointestinal symptoms in healthy adults (Hanifi et al., 2015; Kalman et al., 2009; Culpepper et al., 2016). The present study provides supporting data that the tool is sufficiently sensitive to detect differences in healthy individuals. A lower rating of the abdominal pain scale of the GSRS was demonstrated for *L. johnsonii* N6.2 versus placebo. The individual symptom data suggests that *L. Johnsonii* N6.2 demonstrates a beneficial effect by reducing stomach ache or pain in the healthy adults studied. The results of the present study suggest that use of *L. johnsonii* N6.2 in individuals with abdominal pain, such as those with IBS.

Of interest is the effectiveness of *L. johnsonii* N6.2 on lessening the daily symptom reporting of headache and cramping.

In BB-DR rats, the mechanism of *L. johnsonii*-host interactions related to prevention of TID may involve downregulation of the production of kynurenine and increasing tryptophan flux toward the synthesis of serotonin (Valladares et al., 2013). To evaluate whether these fluctuations in tryptophan metabolites observed in rats could be used as a marker of *L. johnsonii* activity in humans, the levels of tryptophan metabolites were determined in serum throughout the study. A strong trend toward decreased serum levels of kynurenine along with increased amounts of tryptophan was observed in a subgroup of participants who consumed *L. johnsonii* N6.2 and exhibited an increase of LAB CFU/g stool over the treatment period. These fluctuations in the metabolites were directly related to IDO, which has been associated with an important role in immune regulation and has been related to the modulation of chronic inflammation, as well as allergic and autoimmune disorders.

In this study, we determined the concentrations of several intermediates in the tryptophan degradation pathway. A significant increase in the tryptophan concentrations and a decrease in the tryptophan/kynurenine ratio was observed after the wash-out period (12 weeks) in the *L. johnsonii* N6.2 group. The symptom of anxiety was significantly lower in the *L. johnsonii* group during the washout period. This symptom has been associated with decreased levels of serotonin (Young, 2007; Rao et al., 2009), and since we observed differences in the symptom score in the *L. johnsonii* group, the modulation of IDO activity by the probiotic may have channeled the tryptophan concentrations towards the production of serotonin.

The administration of probiotic *L. johnsonii* N6.2 resulted in a progressive increase in the frequencies of monocytes and NK cells (specifically the activated NK CD16$^+$CD56$^{hi}$ subset), reaching statistical significance after the wash-out period. However, B cells or DCs did not show changes between the groups during the treatment period or after wash-out. NK cell activation may result from cell-to-cell contact as result of NK/DC crosstalk (Piccioli et al., 2002) or it may result from to the direct interaction of *L. johnsonii* N6.2 associated-molecules, such as lipids or DNA, with NK cells. TLR9 activation is a likely mechanism.

In this study, we observed a significant increase in the activated HLA-DR$^+$CD38$^+$ Th1 population after the 8 weeks of treatment and after the wash-out (12 weeks).

Notably, we observed significant changes in most CD8$^+$ T cells subsets: Tn, Tcm, Tem and Temra. Among them, activated CD38$^+$HLA-DR$^+$ CD8$^+$ T cells increased significantly at 8 weeks and after wash-out (12 weeks). These results are in agreement with the activation of Th1 responses mediated by NK cells. We observed that the populations remained either decreased or increased after the washout period. These observations were positively correlated with a significant decrease in CD279(PD-1)$^+$ and CD185 (CXCR5)$^+$ CD8$^+$ Tem in the *L johnsonii* N6.2 group after 8 weeks of treatment. These results indicate that *L. johnsonii* N6.2 may reduce apoptosis of memory CD8$^+$ T cells.

In summary, we identified several systemic biomarkers that can be utilized to follow the efficacy of *L. johnsonii* N6.2 consumption in healthy subjects.

In certain aspects, the invention provides following embodiments:

Embodiment 1

A probiotic composition comprising *Lactobacillus johnsonii* N6.2 and pharmaceutically acceptable carrier.

Embodiment 2

The probiotic composition of embodiment 1, wherein the composition is a food.

Embodiment 3

The probiotic composition of embodiment 1 or 2, wherein the food is a fermented food.

Embodiment 4

The probiotic composition of any preceding embodiment, wherein the composition is a dried powder.

Embodiment 5

The probiotic composition of embodiment 4, wherein the dried powder is encapsulated in a capsule.

Embodiment 6

The probiotic composition of embodiment 5, wherein the capsule is acid resistant.

Embodiment 7

The composition of claim 6, wherein the capsule contains about 10$^8$ CFU of *Lactobacillus johnsonii* N6.2.

Embodiment 8

A method for alleviating symptoms of indigestion, abdominal pain or cephalic syndrome in a subject, comprising administering to the subject a composition comprising an effective amount *Lactobacillus johnsonii* N6.2.

Embodiment 9

The method of embodiment 8, wherein the subject has not been diagnosed with type 1 diabetes.

Embodiment 10

The method of embodiment 8 or 9, comprising orally administering the composition to the subject.

Embodiment 11

The method of any of embodiments 8 to 10, wherein the composition is a food.

Embodiment 12

The method of embodiment 11, wherein the food is a fermented food.

Embodiment 13

The method of any of embodiments 8 to 12, wherein the composition is a dried powder.

Embodiment 14

The method of embodiment 13, wherein the dried powder is encapsulated in a capsule.

Embodiment 15

The method of embodiment 14, wherein the capsule is acid resistant.

Embodiment 16

The method of embodiment 15, wherein the capsule contains about 10$^8$ CFU of *Lactobacillus johnsonii* N6.2.

Embodiment 17

The method of any of embodiments 8 to 16, wherein said administering increases serum tryptophan levels in the subject.

Embodiment 18

The method of any of embodiments 8 to 17, wherein said administering decreases kynurenine:tryptophan (K:T) ratio in the subject.

Embodiment 19

The method of any of embodiments 8 to 18, wherein said administering increases circulating levels of Immunoglobulin A (IgA) in the subject.

The pharmaceutically acceptable carriers are intended to protect the bacteria from adverse environmental conditions that may kill the bacteria in the absence of the pharmaceutically acceptable carriers. Such carriers include biodegradable and edible polymers and other known ingredients that protect bacteria.

In preferred embodiments, the food is a fermented food, such as fermented milk products (yogurt, cheese) or fermented vegetables (sour kraut, kimchi, pickles, etc.) Dried powder containing the bacteria can be lyophilized powder.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Efficacy of *L. johnsonii* N6.2 Consumption in Healthy Subjects

A double-blind, randomized clinical trial was undertaken to evaluate subject responses to the consumption of *L. johnsonii* N6.2 in 42 healthy individuals with no known risk factors for T1D. The administration of *L. johnsonii* N6.2 did not modify the CMP or CBC of participants suggesting general safety. In the *L. johnsonii* N6.2 group, serum tryptophan levels increased resulting in a decreased K:T ratio. *L. johnsonii* N6.2 administration significantly decreased the occurrence of abdominal pain, indigestion and cephalic syndromes. Interestingly, immunophenotyping assays revealed that monocytes and natural killer (NK) cell numbers were durably increased significantly after wash-out (12 weeks). Moreover, an increase of circulating effector Th1 cells ($CD45RO^+CD183^+CD196^-$) and cytotoxic $CD8^+$ T cells was observed

Methods

Subjects

Forty-two healthy adults (F=30, M=12; mean age±SD=23.2±5.5 years) participated in the study. Participants were recruited from the community and the University of Florida campus in Gainesville, FL, USA. Exclusion criteria included: gastrointestinal disease (gastric ulcers, Crohn's, ulcerative colitis, etc.), chronic disease such as diabetes, kidney disease and heart disease; current or past treatment for immune-compromising diseases or conditions; currently working or living with an immunocompromised person; currently taking medications for constipation, diarrhea or a psychological disorder (depression, anxiety, insomnia etc.); antibiotics within the past 4 weeks prior to randomization; currently taking a probiotic supplement and unwilling to discontinue a minimum of 2 weeks prior to the study start; current smoker; pregnant or lactating or a female who plans to become pregnant in the next 6 months; and a known allergy to milk. Inclusion criteria included men and women 18-50 years of age and approval to participate following screening blood work and physical examination by the advising physician.

Experimental Design

In a double-blinded study, healthy volunteers were randomly and assigned to one of two treatments, *L. johnsonii* N6.2 at $5 \times 10^8$ CFU per capsule or placebo (skim milk) capsule for 8 weeks in a parallel design. Prior to treatment, there was a 1-week pre-baseline period, and treatment was followed by a 4-week wash-out period. One week prior to randomization, consented participants underwent a physical examination and were screened via a CMP, and females received a pregnancy test. During pre-baseline, intervention and wash-out periods, participants completed a daily online questionnaire, reporting on: study supplement intake, hours of sleep, bowel movement frequency, gastrointestinal symptoms, general wellness, and medication use. In addition, participants completed the GSRS, and quality of life was assessed with the quality of life questionnaire, QualityMetric's SF-36v2® on a weekly basis. At the randomization appointment, height, weight, vitals (blood pressure, heart rate) and demographic information was obtained. Two 24-hour diet recalls (by telephone) were completed during the baseline, intervention, and wash-out periods. CMP and CBC were assessed at baseline, during weeks 2, 4 and 8 of the study intervention, and during wash-out. An additional pregnancy test was given during week 4 of the intervention phase. At a final appointment, participants returned any unconsumed supplements.

*Lactobacillus johnsonii* N6.2 Culture and Capsules Elaboration

*L. johnsonii* N6.2 was grown in MRS medium (peptone 10 g, beef meat powder 8 g, yeast extract 4 g, glucose 20 g, $K_2HPO_4$ 2 g, sodium acetate 5 g, ammonium citrate tribasic 2 g, $MgSO_4.7H_2O$ 0.2 g, $MnSO_4.H_2O$ 0.05 g, tween80 1 g; final volume of 1 L with DI water) at 37° C. for 16 hours under microaerophilic conditions. Cells were pelleted by centrifugation at 6000 g for 20 minutes at 4° C. and washed twice with BAM R61 0.02M phosphate buffer pH 7.3 (Bacteriological Analytical Manual, 8th Edition, Revision A, 1998). The cell pellet was resuspended in sterile reconstituted food grade skim milk at 100 g/L (Real Food, IL, USA), transferred to sterile bags (Whirl-Pak, USA), and frozen at −80° C. for at least 2 hours. The frozen samples were freeze-dried (LabConco FreeZone, LabConco Corp., MO, USA) for 48 hours. The dried powder was saved at 4° C. until capsule filling. Acid resistant capsules (AR Caps, Size #1, CapsCanada, Pompano Beach, Fla., USA) were filled using a sterilized Profiller (Torpac®, NJ, USA) with 160±20 mg ($1 \times 10^9$ CFU/g) of the freeze-dried preparation of *Lactobacillus johnsonii* N6.2 in skim milk (Real Food, IL, USA). Lyophilized skim milk (160 mg) in identical capsules was used as the placebo. The study capsules were provided in bottles labeled with treatment codes by a study collaborator who did not have contact with study participants.

Stool Sample Collection and Transit Survival of *L. johnsonii* N6.2

Single stools were collected using a commode specimen collection system (Fisher Scientific, Pittsburgh, Pa., USA) during the last 2 days of pre-baseline, during weeks 2, 4 and 8 of the intervention, and during wash-out. Participants were instructed to place the stool containers on ice immediately after defecation and deliver samples to study personnel within four hours of defecation. Samples were homogenized and fractionated on sterile vials (approx. 1.0 g/vial) and saved at −80° C. until use. Fresh samples (approximately 1 g) were immediately diluted (dil. 1/10 w/v) in phosphate buffer solution (pH: 7.3-7.4), and serial dilutions were made and plated on MRS agar media (pH; 5.5±0.1). Plates were incubated for 48 hours under microanaerobic conditions. Values were referred as CFU per wet gram stool (CFU/g). The identity of *L. johnsonii* N6.2 was confirmed by PCR amplification of the strain specific gene T285_00345 gene (Leonard et al., 2014).

Blood Sample Collection and CMP

From fasting blood samples, serum (Red top Tube, BD, USA) and plasma (EDTA Purple top Tube, BD, USA) were collected. The CMP was obtained from serum samples, evaluating glycaemia (glucose level); kidney function (creatinine and urea level); and liver function (GPT, GOT, alkaline phosphatase and bilirubin level). The analysis was performed by Vista Clinical Diagnostics, Clermont, Fla., USA. Additionally, plasma and serum samples were aliquoted, flash frozen in liquid nitrogen and stored at −80° C. for further assays. Serum insulin levels were quantified by ELISA (eBioscience, CA, USA).

IDO Activity: Tryptophan Metabolites Pathway

Quantification of tryptophan catabolites and other metabolites in blood plasma samples (i.e. tryptophan, kynurenine, kynurenic acid, xanthurenic acid, serotonin and anthranilic acid) were performed using global high performance liquid chromatography and mass spectrometry (LC-HRMS/HRMS) at the Southeast Center for Integrated Metabolomics Biomedical Mass Spectrometry Core of the University of Florida.

Cytokine Determinations

The following ELISA kits were used: IL-2, IL-6, and TNF-α from eBioscience (CA, USA); IFN-γ and IFN-α from Abcam (MA, USA); IL-2SsRα from BD (NJ, USA); and CRP from Cayman Chemical (MI, USA) following the manufacturers' instructions.

Flow Cytometry

Direct immunofluorescence staining of PBMCs was done by mixing 200 µL of whole blood samples with 20 µL of specific antibody and fluorescence minus one (FMO) control master mixes (BD Bioscience, USA) in 5 mL polystyrene round bottom tubes (BD Falcon®). The PBMC populations evaluated were: B cells, DCs, Monocytes and NK cells (DCMoNKcells/FM-APC), T cells (Tcell/FM-FITC & FM-APC), Tregs (Treg/FM-FITC & FM-APC), Tfh (Tfh/FM-APC) and Teff (Teff/FM-FITC & FM-APC) as previously described (Maecker et al., 2012). The mixture was vortexed and incubated for 30 min at room temperature and protected from light. Afterwards, 2 mL of Fix/lyse 1× (eBioscience, USA) was added and incubated at room temperature for 5 min. Successive washing/centrifugation (5 min, 450 g) steps with 4 mL of staining buffer were performed until color completely faded. The pellet was resuspended in 3 mL of staining buffer, briefly vortexed and stored at 4° C. The samples were briefly mixed before acquisition within 48 h on a BD Fortessa cytometer, and data were analyzed by FlowJo™.

Extraction of Fecal Microbiota

DNA was extracted from fecal samples and preserved at −80° C. using the PowerFecal® DNA isolation kit (MoBio Lab, Inc. USA) with the following modification. 250 mg of fecal sample were homogenized in 750 µL of bead solution and 100 µL of Protease from *Streptomyces griseus* 20 mg/mL (Sigma-Aldrich, Steinheim, Germany) were added. The mixture was incubated at 37° C. for 15 min and, then the samples were processed according to the manufacturing protocol. In the elution step, the DNA was collected in 70 µL of water and quantified. The DNA concentration was standardized to 1 ng/µL before the amplification of the V4 region using primers for paired-end sequencing on the Illumina MiSeq platform as described earlier (Caporaso et al., 2012).

Microbiota Analysis

Clustering of Operational Taxonomic Units (OTUs) at 97% similarity was performed with the subsampled open-reference OTU picking method (Rideout et al., 2014), with no removal of singletons. The Greengenes reference dataset version 13.8 (DeSantis et al., 2006) was used as the reference for OTU picking and for taxonomy assignment with uclust (Edgar et al., 2010). OTUs identified as mitochondrial DNA or as chloroplasts were removed from further analyses.

Statistics

Unless otherwise noted, statistical analysis was performed using JMP Pro software (SAS Institute, Cary, N.C., USA). Multivariate analysis was performed by 2-way analysis of variance (ANOVA) with a post hoc Tukey's honestly significant difference test. Bivariate analysis was performed using Student's t tests. Numerical data are summarized as means±se. Significance was defined as $p<0.05$.

Analyses of Surveys

For each of the response variables a repeated measures analysis was performed by fitting a linear mixed model that considered the repeated nature of the data. The fitted model had the following form: $y=\mu+gender+supp+group(supp)+e$ where µ is the overall mean, gender is the gender effect, supp is a diet supplementary effect, group(supp) corresponds to the combination of measurement week within a diet supplement effect, and e corresponds to an error term, where measurements from the same individual were correlated using an unstructured error with a different correlation for each pair of time points and a different error variance for each time point. The models were fitted using SAS v. 9.4 with the procedure MIXED and degrees of freedom were adjusted using the Kenward-Rogers correction. Comparisons of means for the diet supplement levels at a given week were obtaining constructing specific contrasts, and for all tests a significance level of 5% was considered.

Analyses of Immune Cells

For each of the response variables a repeated measures analysis was performed by fitting a linear mixed model that considered the repeated nature of the data. The fitted model had the following form: $y=\mu+\beta^*x0+gender+supp+group+time+supp^*time+group^*time+supp^*group+supp^*group^*time+e$ where µ is the overall mean, $\beta^*x0$ is the regression coefficient associated with the covariate for initial measurement $\beta^*x0$, gender is the gender effect, supp is a diet supplementary effect, group is the group effect, and time is the time of measurement. The other terms are the two- and three way interactions. Also, e corresponds to an error term, where measurements from the same individual were correlated using an unstructured error with a different correlation for each pair of time points and a different error variance for each time point. The models were fitted using SAS v. 9.4 with the procedure MIXED and degrees of freedom were adjusted using the Kenward-Rogers correction. Comparisons of means for a given model term were obtained with the least significance difference (LSD), and for all tests a significance level of 5% was considered.

Analysis of Microbiota

Community structure was analyzed in R with phyloseq (McMurdie and Holmes, 2013) and plotted with ggplot2 (Wickham, 201109). Analysis of similarities (ANOSIM) and Permutational Multivariate Analysis of Variance (PER-MANOVA) was performed in R using VEGAN v2.0-8 (Dixon, 2003). Differences in taxonomic profiles were analyzed by Welch's t-test (for two groups) or by ANOVA (for multiple groups) with Tukey-Kramer post-hoc tests with STAMP (Parks et al., 2014).

Example 2—The Administration of *L. johnsonii* N6.2 Decreases Indigestion, Abdominal Pain, & Cephalic Syndrome Scales Forty-two healthy adults [female (F)=30, male (M)=12; mean age ±SD=23.2±5.5 years] participated in the study. Participants were recruited from the community and the University of Florida campus in Gainesville, FL, USA in accordance with an Institutional Review Board (IRB) approved study at the University of Florida. Of the 92 individuals initially screened and assessed for eligibility, 50 were consented, and 42 randomized to the treatment groups (FIG. 1) in a double-blind parallel study design. Table 1 summarizes the characteristics and compliance of the subjects that participated in the study.

The analysis of the hemogram and comprehensive metabolic panel (CMP) data showed no statistically significant differences between the *L. johnsonii* N6.2 and placebo groups (Table 2). The only parameter that showed statistical significance after 8 weeks of treatment was total bilirubin values (placebo=0.54±0.05 versus *L. johnsonii* N6.2=0.70±0.05, p<0.05); however, both groups were within the normal range of 0.2-1.9 mg/dL. These differences were not observed after the wash-out period (12 weeks). No statistically significant differences were observed in both control and treatment cohorts for indicators of kidney and liver function (Table 2). As expected, no alterations in the circulating levels of insulin and C reactive protein (CRP) were observed in the probiotic group at 8 weeks or 12 week compared to placebo. Based on these results, the consumption of *L. johnsonii* N6.2 was well-tolerated without apparent risks for the subjects or deviations from the normal reference ranges of standard clinical assessments.

General digestive health was next assessed over the course of the trial. During pre-baseline, intervention and wash-out periods, participants completed a daily online questionnaire reporting study supplement intake, hours of the sleep, bowel movement frequency, gastrointestinal symptoms, general wellness, and medication use. Of the five domains of the weekly gastrointestinal symptom rating scale (GSRS) questionnaire, indigestion (p<0.05) and abdominal pain (p<0.05) were significantly lower among *L. johnsonii* N6.2 treated subjects during treatment weeks 2 to 8, and during wash-out weeks 1 to 4 compared to placebo (Table 3). Syndrome scores from the daily questionnaire indicated that cephalic syndrome, including the symptoms of headache and dizziness, was significantly lower (p<0.05) for *L. johnsonii* N6.2 versus placebo for treatment weeks 2 and 4 to 8. The gastrointestinal distress syndrome was lower (p<0.05) for *L. johnsonii* N6.2 versus placebo during most treatment weeks and neared significance at baseline (p=0.05). Interestingly, the probiotic group showed a significant decrease (p<0.05) in the epidermal syndrome at the end of the wash-out period (Table 4).

Stomach ache or pain as an individual symptom was significantly lower in the group receiving *L. johnsonii* N6.2 during treatment weeks 1 to 8 compared to the placebo group, with a similar trend at baseline (p=0.06) (Table 5). Bloating as an individual symptom was lower (p<0.01) in *L. johnsonii* N6.2 versus placebo at baseline and during most treatment and washout weeks (Table 5). Administration of *L. johnsonii* N6.2 also resulted in lower individual daily symptoms of cramping, abdominal noises, and headache for most treatment weeks. Furthermore, a significant decrease in the anxiety symptom was observed after the wash-out period in the probiotic group was observed (Table 5). The anxiety changes may have affected the psychology syndromes where a trend to decrease (p<0.1) during the wash-out was observed (Table 4).

Example 3—*L. Johnsonii* N6.2 Survives Human Gastrointestinal Transit

Gastrointestinal transit survival of *L. johnsonii* N6.2 was evaluated by following the total Colony Forming Units (CFU)/g of stool counts of lactic acid bacteria (LAB) in fresh fecal samples. Additionally, the presence of *L. johnsonii* N6.2 was confirmed by RT-PCR of the T285_00345 gene.

Figure 2A:
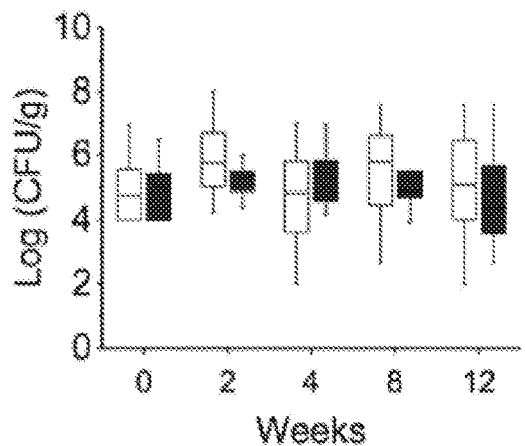
FIGS. 2A-2F show determination of total lactic acid bacteria and *L. johnsonii* N6.2 (Ljo) in stool samples. In placebo and Ljo groups it was determined: 2A) Total number of LAB (Log CFU/g). Based on the numbers of LAB obtained, three subgroups were defined: a—High LAB, b—Low to high LAB and c—Low LAB. Results are shown in 2B and 2C, for the Ljo or placebo treatment groups, respectively. 2D) The presence of Ljo was confirmed by performing qRT-PCR of the T285_00345 gene and expressed as genomic equivalents. The data was further stratified based on the determination of total LAB numbers for the Ljo (2E) and placebo (2F) treatment groups. * indicates statistical differences ($p<0.05$) between the groups and time points shown in 2E and 2F using analysis of variance. Comparison of the treatment combinations was performed by least significance difference with a significance level of 5%.
Figure 2B:
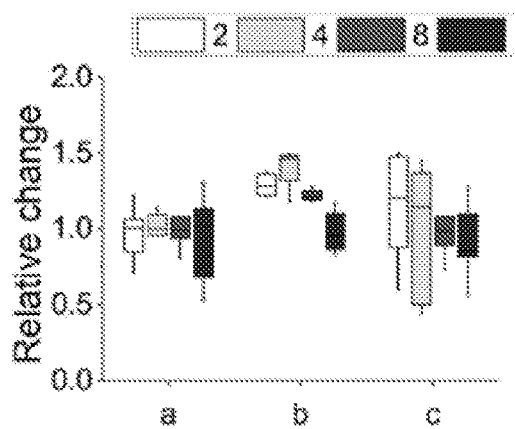
Figure 2C:
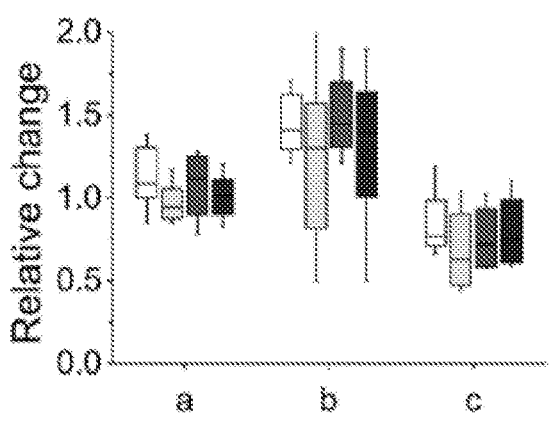

Overall, a large variability in the amount of the total CFU/ml of LABs was observed between subjects (from $10^2$ to $10^8$ CFU/g stools) at T0, and no significant changes were observed over time either in the placebo or in the *L. johnsonii* N6.2 treatment group (FIG. 2A). However, it was possible to observe three groups of subjects within each treatment, a) subjects with high counts of LAB throughout the study ($>10^5$ CFU/g), b) a group that at T0 showed low concentrations of LAB that increased over time (from $10^4$ to $10^8$ CFU/g) and c) subjects with low counts of LAB throughout the study ($<10^5$ CFU/g). To quantify the variation of the LAB population, the log CFU/g values for T0 was subtracted at each time point and expressed as relative change (log CFU/g at each time point/log CFU/g at T0). For subjects with consistently high or low LAB populations (groups a and c), the relative fold change in LAB was 1.0±0.11 and 0.8±0.02, respectively, in the probiotic group (FIG. 2B). Similar results were obtained in the placebo group (FIG. 2C). As expected, subjects in group b that received *L. johnsonii* N6.2 capsules displayed the highest relative change in LAB counts (FIG. 2B). After the wash-out period, the LAB counts appeared to return to baseline levels (FIGS. 2B-2C). These results suggest that *L. johnsonii* N6.2 survived the transit through the gastrointestinal system and may potentially colonize the gut.

Figure 2D:
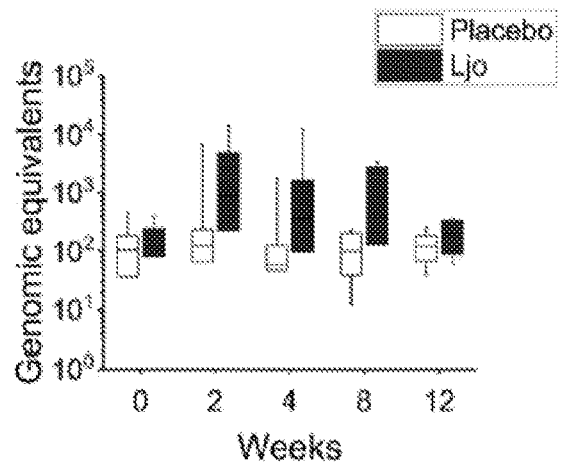
Figure 2E:
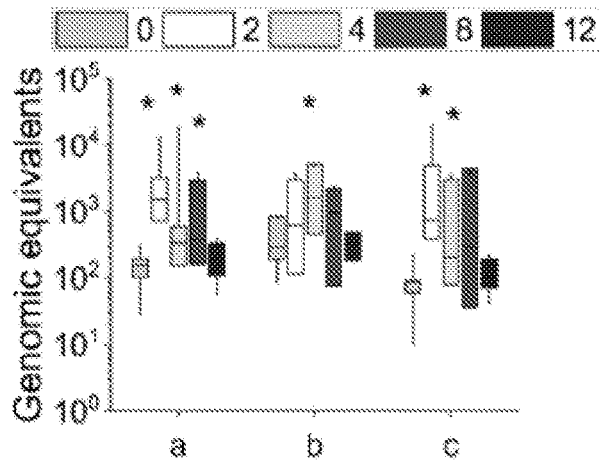
Figure 2F:
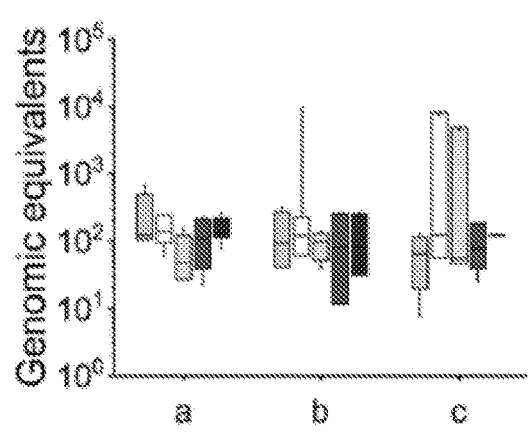

To verify this hypothesis, the presence of *L. johnsonii* N6.2 was confirmed using specific RT-PCR of the T285_00345 gene and expressed as genomic equivalents/100 ng of DNA (FIG. 2D). This gene was found in the genome of *L. johnsonii* N6.2 but not in others in the NCBI database. It was found that the T285_00345 gene gave background amplification on the placebo-treated group (FIG. 2F) while a significant increase in genomic equivalents over time were observed in the *L. johnsonii* N6.2 group (FIG. 2E). Interestingly, the presence of *L. johnsonii* N6.2 was confirmed in all the subgroups (a, b and c) independently of the total LAB counts (see FIGS. 2E-2F). However, after wash-out, the genomic equivalents of in *L. johnsonii* N6.2 group were similar to time 0 or below the detection limit.

Example 4—*L. johnsonii* N6.2 Modulates the Concentration of Metabolites in the IDO-Dependent Pathway in Healthy Subjects The administration of *L. johnsonii* N6.2 to BB-DP rats was previously reported to result in decreased expression of IDO and, consequently, changes in the K:T ratios in peripheral serum (Valladares et al., 2013). Here, the impact of *L. johnsonii* N6.2 on IDO activity was evaluated by quantifying plasma levels of the following metabolic intermediates in the tryptophan pathway: tryptophan, kynurenine, serotonin, xanthurenic acid, anthranilic acid and kynurenic acid. Samples taken at different time points (0, 8 and 12 weeks) were quantified using liquid chromatography-mass spectrometry (LC-HRMS/HRMS) (Table 6). Based on findings in rodent studies, it was expected that a decrease in IDO activity or expression would increase the concentration of tryptophan, while decreasing the concentrations of kynurenine, xanthurenic acid, anthranilic acid and kynurenic acid associated also to a possible increase in serotonin levels (Valladares et al., 2013). For each of the metabolites, no significant differences were observed between the treatment groups during the treatment period. Similarly, the K:T ratio was not affected, being similar for both groups during treatment with placebo or *L. johnsonii* N6.2 (Table 6).

Figure 3A:
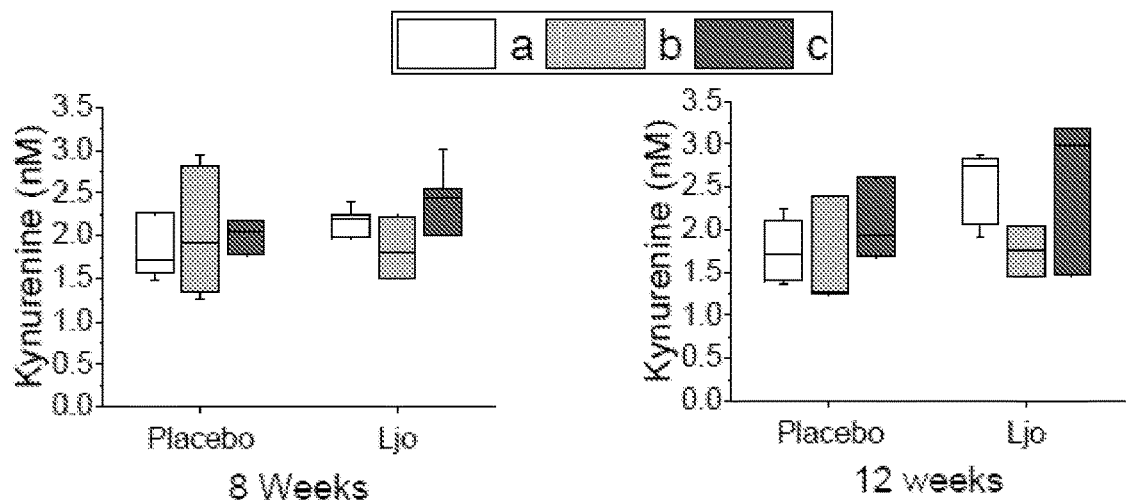
FIGS. 3A-3C show peripheral tryptophan and kynurenine concentration in plasma of healthy subjects. The concentrations of kynurenine (3A) and tryptophan (3B) were determined by LC/MS after 8 or 12 weeks in the placebo or *L. johnsonii* N6.2 (Ljo) treatment groups. In 3C is shown the kynurenine:tryptophan (K:T) ratio. The concentration of the metabolites shown has been normalized to the concentration found at T0 for each subject. The results obtained were further stratified based on the number of LAB present as described in the results section. a)—High LAB; b)—Low to high LAB and c)—Low LAB.
Figure 3B:
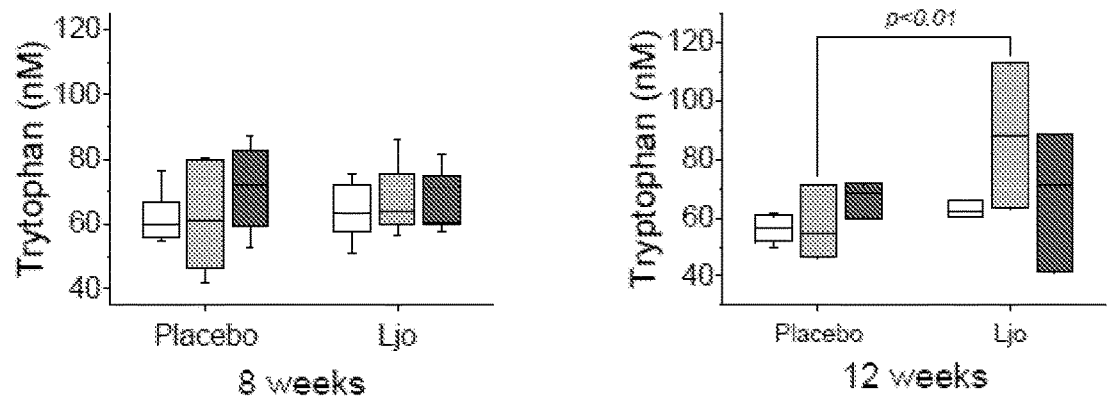
Figure 3C:
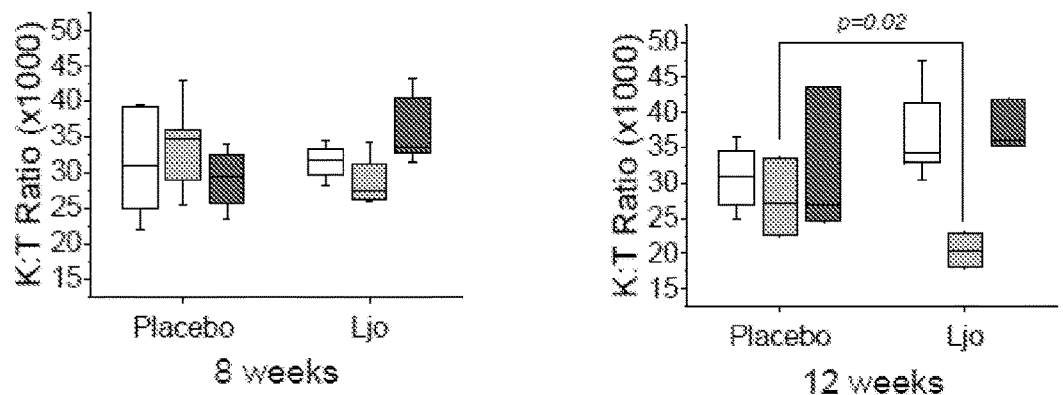

Similar statistical analyses of the metabolic intermediates were also conducted considering the LAB counts (groups a, b or c as described above). After 8 and 12 weeks, the kynurenine values did not change significantly (p>0.1) in the different subgroups (FIG. 3A). After 8 weeks (last day of treatment), a slight increase in the tryptophan concentration was observed which correlated with a decrease in the K:T ratio in probiotic versus placebo treated group b subjects (low to high LAB counts), although statistical significance was not reached (p=0.17 and p=0.13, respectively) (FIGS. 3B-3C). Interestingly, at 12 weeks (after 4 weeks of washout) the changes in tryptophan and K:T ratio reached statistical significance with p<0.01 and p<0.05, respectively (FIGS. 3B-3C). These results suggest that the effects of *L. johnsonii* N6.2 supplementation may take longer than 8 weeks to be quantified.

The fact that the expected modulation of the tryptophan pathway was only observed in one group of subjects (low to high LAB counts), suggests that the effects of *L. johnsonii* N6.2 supplementation may require an intestinal environment that is permissive to microbe colonization over time. These results indicate that the counts of LAB during baseline may also be used as biomarkers to predict responders from non-responders in a heterogeneous population.

Example 5—*L. johnsonii* N6.2 Supplementation Alters the Frequency of Immune Subsets in Peripheral Blood The impact of *L. johnsonii* supplementation on the immune system was evaluated by flow cytometry of peripheral blood mononuclear cells (PBMCs) as described by Maecker et al. (2012). The identification of immune cell subsets was performed by eight-color antibody staining at T0, after 8 weeks of treatment or after the wash-out period (12 weeks). Six antibody staining panels were used to differentiate the following immune cell subsets of the innate and adaptive arms of the immune system: (i) B cells, (ii) natural killer (NK), monocytes, and DCs, (iii) naïve and memory T cells, (iv) follicular helper T cells (TfH), (v) differentiated effector T cells (Teff), and (vi) regulatory T cells (Tregs).

(i) B Cell Subsets

Figure 4:
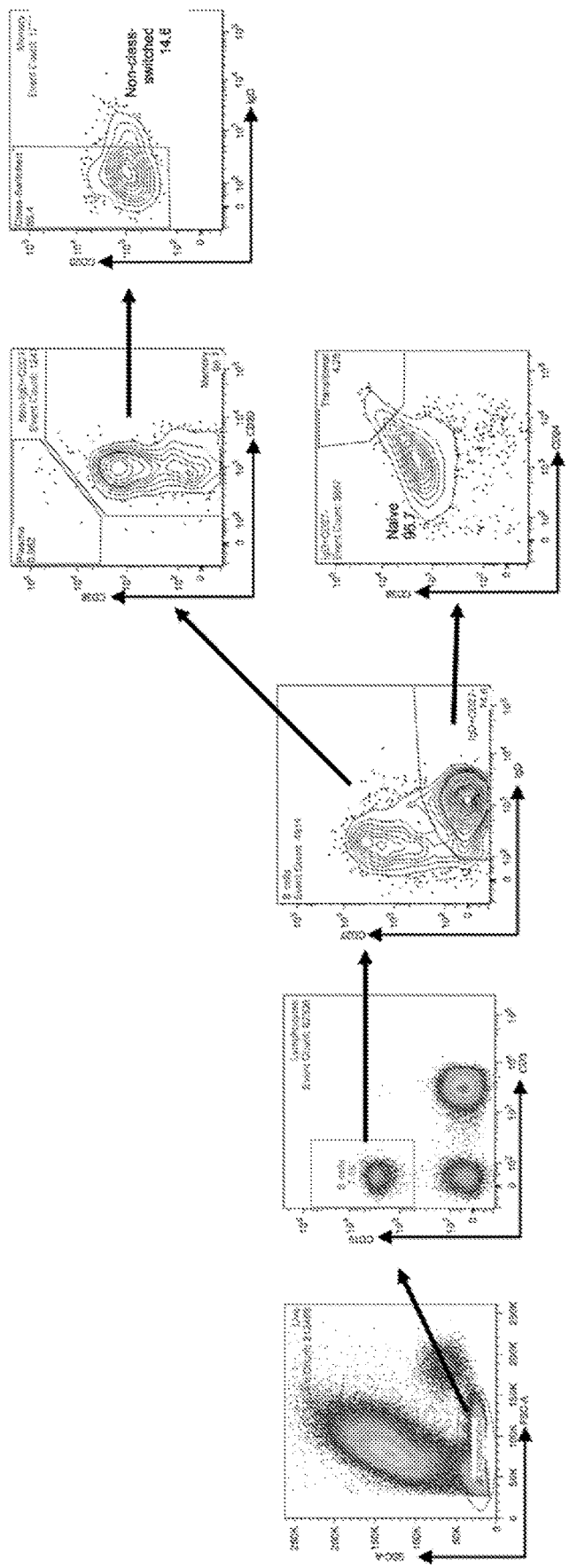
FIG. 4 shows flow cytometry gating strategy for evaluation of the B cells subset in healthy subjects.

From the B cell population ($CD3^-CD19^+$), we analyzed the frequencies of transitional ($CD27\text{-}IgD+CD24^{hi}CD38^{hi}$), naïve ($CD27^-IgD^+CD24^{lo/-}CD38^{lo/-}$), non-class switched memory ($CD20^{hi}CD27^+IgD^+$), class switched memory ($CD20^{hi}CD27^+IgD^-$), or plasmablast ($CD20^{lo/-}CD38^+$) cells (FIG. 4). Analyses of these cell populations either after 8 weeks of treatment or following the wash-out period indicated that no significant changes were observed upon administration of *L. johnsonii*. (Table 7).

(ii) NK, Monocytes and DC Subsets

Figure 5:
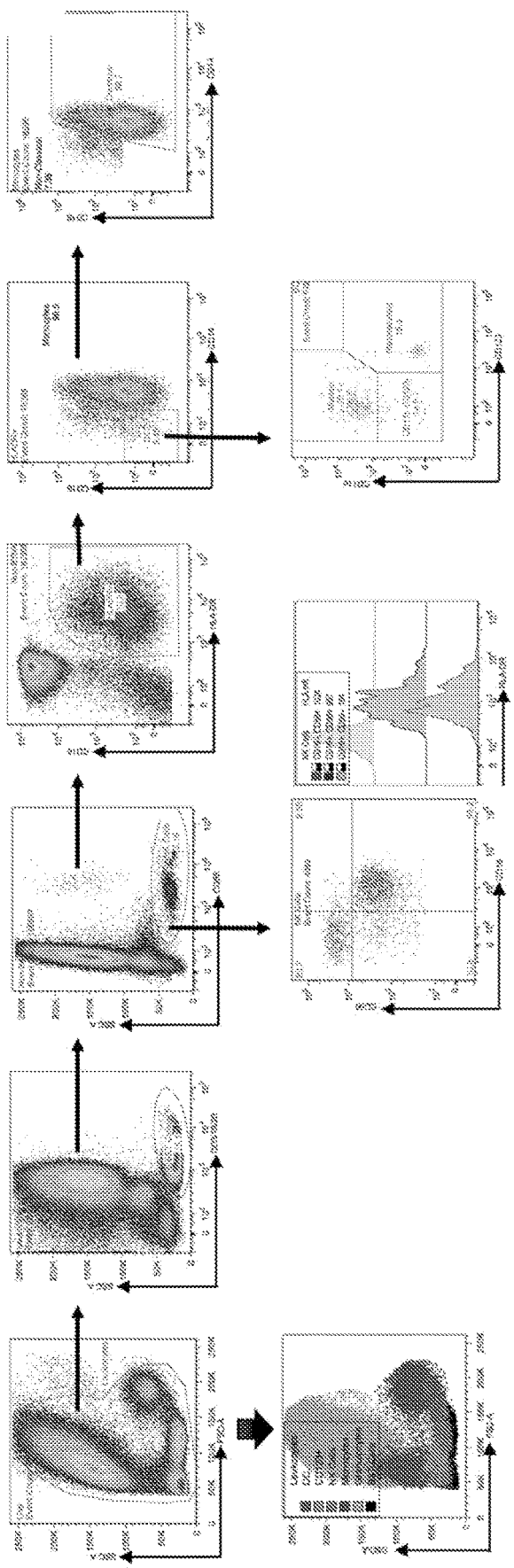
FIG. 5 shows flow cytometry gating strategy for evaluation of the NK, monocytes and dendritic cells subsets in healthy subjects.
Figure 6A:
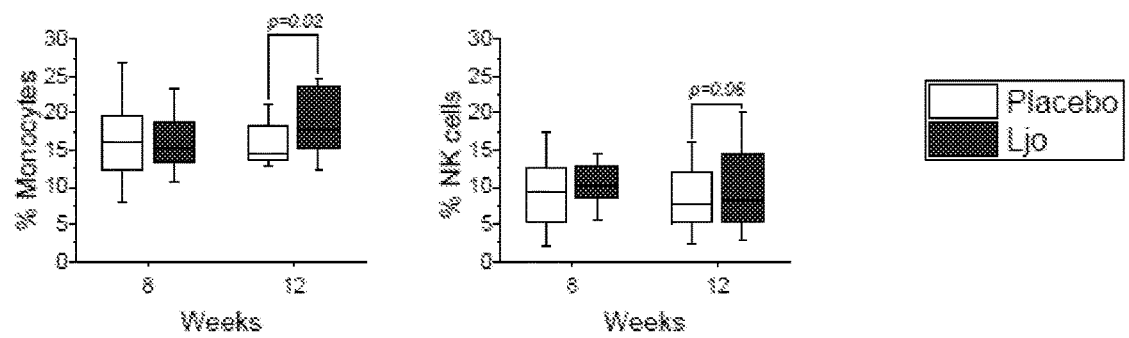
FIGS. 6A-6B show monocytes and NK cells in healthy subjects. 6A) MNC ($CD3^-$ $CD19^-$) were stained with specific antibodies to define monocytes ($CD14^+$) and NK cells ($CD14^-$) in the placebo and in the *L. johnsonii* N6.2 (Ljo) groups. 6B) Expression of HLA-DR (mfi) in different NK cells subset: $CD16^-CD56^{hi}$, $CD16^+CD56^{lo/-}$ and $CD16^+CD56^{hi}$ after 8 weeks of treatment or 12 weeks (4 weeks into the wash-out). The concentration of cells shown has been normalized to the concentration found at T0 for each subject.
Figure 6B:
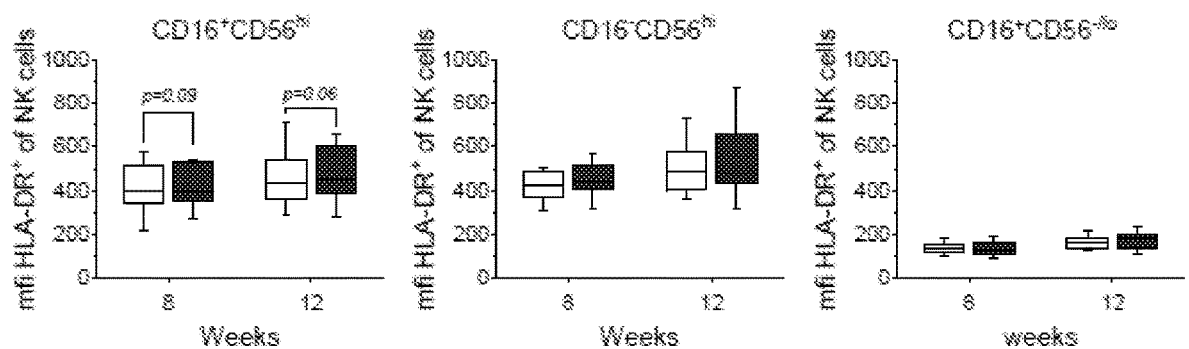

This staining panel facilitated the discrimination of $CD19^-$ cells into monocytes ($CD14^+$), NK cells ($CD14^-CD20^-CD16^+$), myeloid DCs (mDCs) ($CD14^-CD20^-HLA^-DR^+CD11c^+$), and plasmacytoid DCs (pDCs) ($CD14^-CD20^-HLA^-DR^+CD123^+$) (FIG. 5; Table 7). It was found that the numbers of mDCs and pDCs neither changed over time nor as a result of the probiotic supplementation. In contrast, the frequencies of monocytes and NK cells were increased as a result of the probiotic treatment reaching statistical significance at 12 weeks (FIG. 6A). Specifically, a subset of NK cells ($CD16^+CD56^{hi}HLA^-DR^+$) showed a trend toward increasing concentrations after 8 weeks and after the wash-out period (p>0.1, FIG. 6B). The relative frequency of monocytes was not affected significantly after 8 weeks of treatment (p>0.1); however, at 12 weeks, monocyte frequencies increased significantly among probiotic treated subjects (p<0.05) (FIG. 6A; Table 7).

Figure 7:
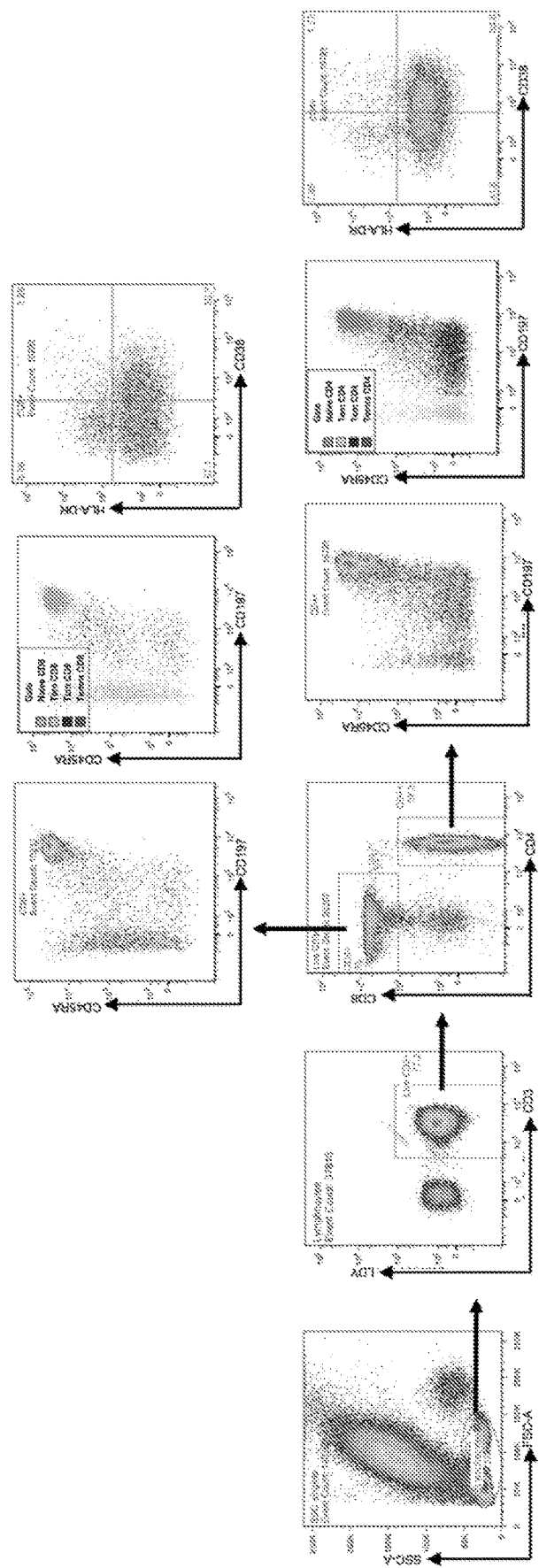
FIG. 7 shows flow cytometry gating strategy for evaluation of nave and memory T cells subsets in healthy subjects.

(iii) Naïve and Memory T Cell Subsets $CD4^+$ and $CD8^+$ T cells were divided into naïve (Tn, $CCR7^+CD45RA^+$), T effector memory (Tem, $CCR7^-CD45RA^-$), T central memory (Tcm, $CCR7^+CD45RA^-$), and T effector memory expressing CD45RA (Temra, $CCR7^-CD45RA^+$) (FIG. 7; Table 8). It was found that the administration of *L. johnsonii* decreased the number of CD4+ cells after 8 weeks of treatment (p<0.05) while after 12 weeks, the numbers of $CD4^+$ cells were similar between the two treatment groups (p>0.1) (FIG. 8A; Table 8). The most notable changes were observed in the $CD8^+CD38^+HLA^-DR^+$ subset after 8 weeks of treatment (p<0.05) (FIG. 8B) and in Temra $CD38^+HLA^-DR^+$ which increased significantly in subjects treated with probiotic compared to placebo (p<0.05) (FIG. 8C). The probiotic treatment decreased the relative amount of naïve $CD8^+$ T cells (p<0.05) while increasing the frequency of $CD8^+$ Tem (p<0.05). The concentrations of both cell types were similar after the wash-out period (FIG. 8B; Table 8).

Figure 9A:
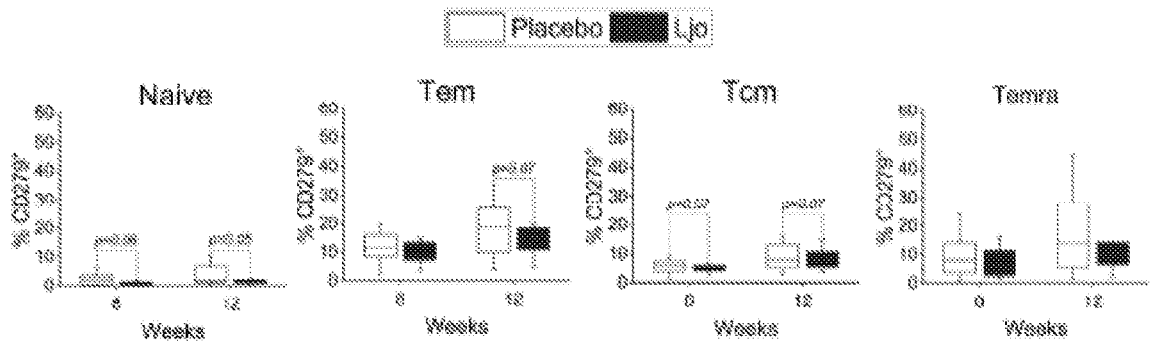
FIGS. 9A-9D show expression of CD185$^+$ and CD279$^+$ on T cells subset. Expression of CD279$^+$ (9A) or CD185$^+$ (9B) on Naïve, Tem, Tcm and Temra CD4$^+$ T cells. Expression of CD279$^+$ (9C) or CD185$^+$ (9D) on Naïve, Tem, Tcm and Temra CD8$^+$ T cells. The number of cells in each population was evaluated for the placebo (white bars) and the *L. johnsonii* N6.2 (Ljo, darker bars) group at 8 and 12 weeks. The concentration of cells shown has been normalized to the concentration found at T0 for each subject.
Figure 9B:
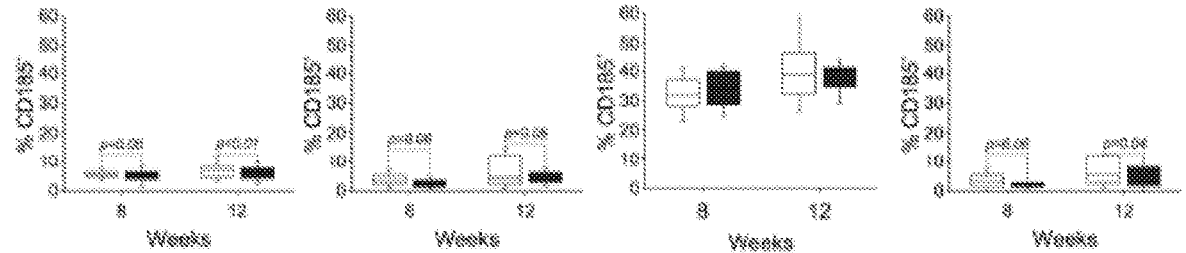
Figure 9C:
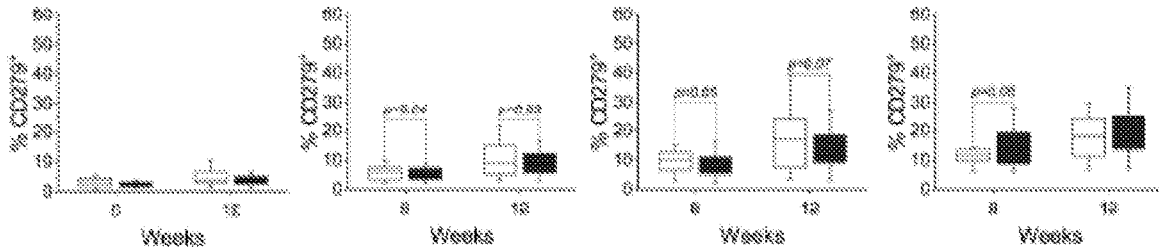
Figure 9D:
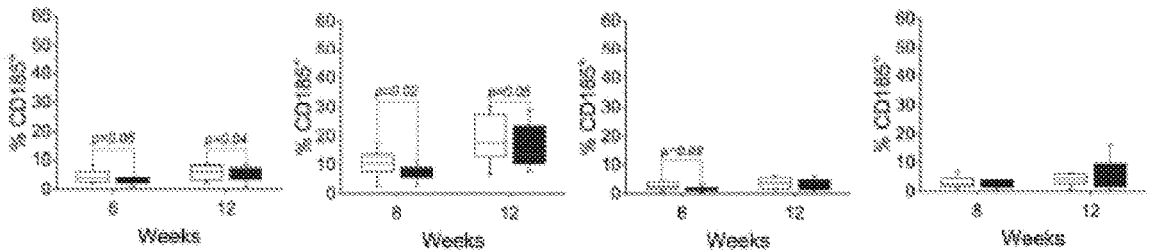

$CD4^+$ T cells also showed strong trends toward decreased CXCR5 and PD-1 expression levels on naïve and Tem subsets as a result of the probiotic supplementation; however, these changes only reached statistical significance after the washout period (for PD-1, p=0.05 and p=0.07; for CXCR5, p<0.01 and p=0.05; respectively) (FIGS. 9A-9B). Furthermore, it was found that the administration of *L. johnsonii* N6.2 for 8 weeks significantly decreased the expression of CD279 (PD-1) on $CD8^+$ Tem and $CD8^+$ Tcm (p<0.05 and p=0.05, respectively) while a trend toward increased the expression of PD-1 on $CD8^+$ Temra cells was also observed (p<0.1). These changes in $CD8^+$ Tem and Tcm cells were sustained after the wash-out period (p<0.05 and p<0.05, respectively) (FIG. 9C). A significant decrease of CD185 (CXCR5) expression on $CD8^+$ naïve and Tem cells was also observed at 8 weeks (p<0.1 and p<0.05, respectively) and sustained even after the wash-out period in both cell populations (p<0.05 and p=0.05, respectively) (FIG. 9D).

Figure 10:
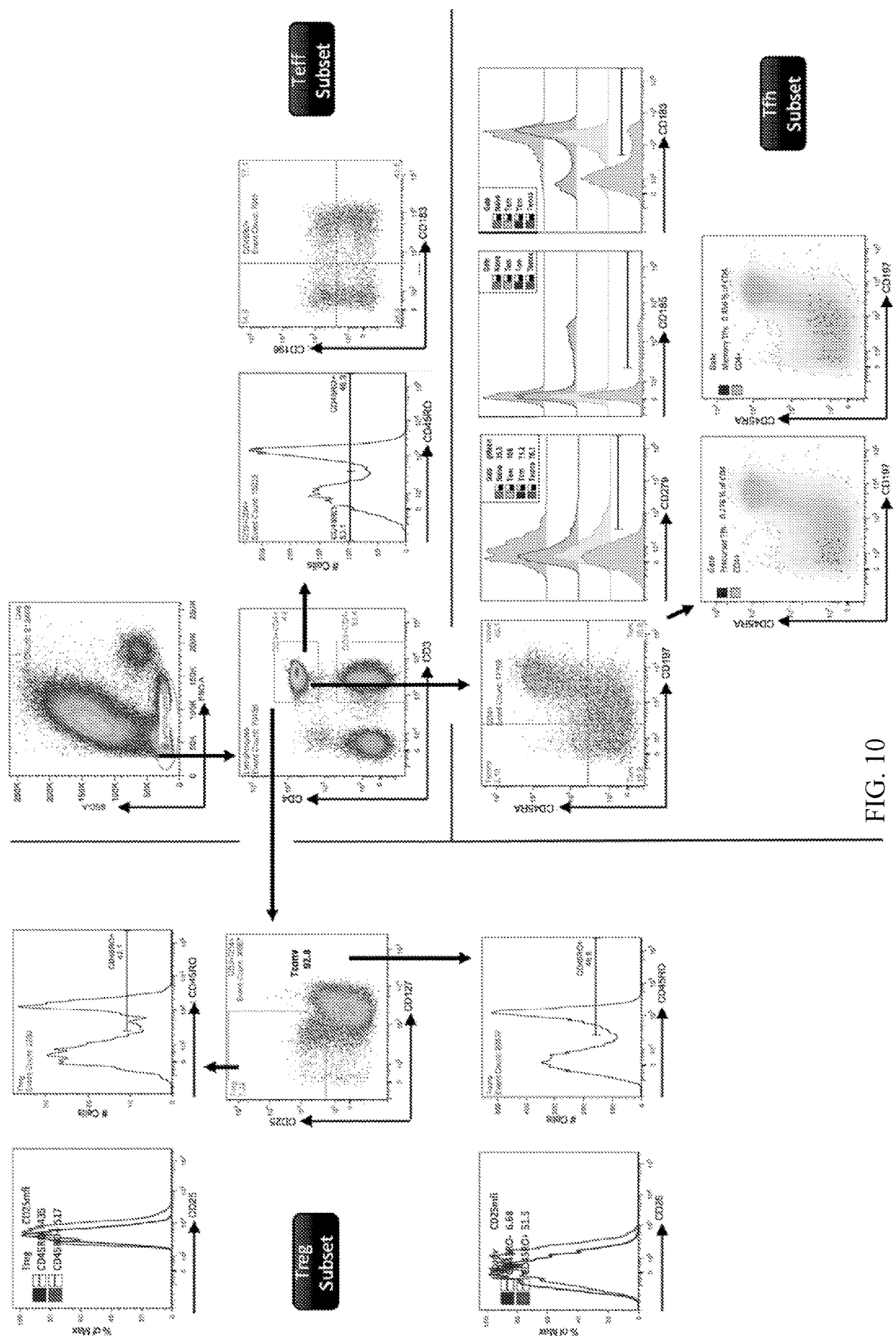
FIG. 10 shows flow cytometry gating strategy for evaluation of differentiated effector T (Teff), T follicular helper, and regulatory T (Treg) cells subsets in healthy subjects.
Figure 11A:
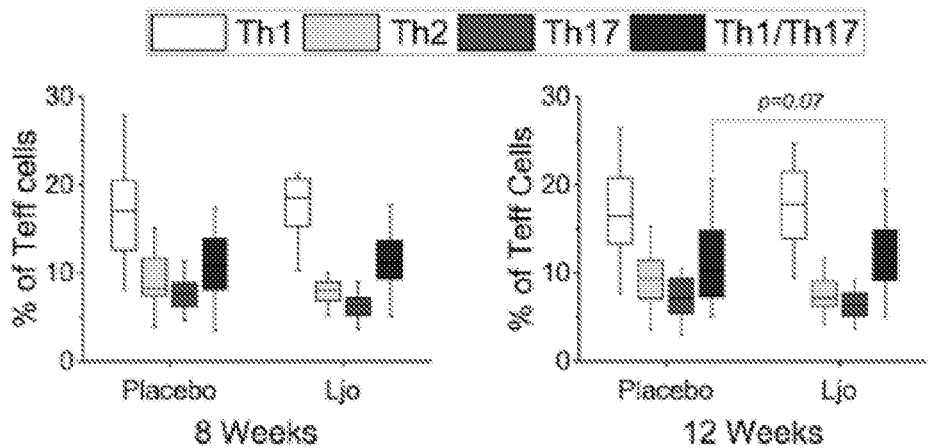
FIG. 11A-11C show T effector cells subset (CD3$^+$CD4$^+$ CD45RO$^+$). 11A) Th1 (CD183$^+$CD196$^+$), Th2 (CD183$^-$CD196$^-$), Th17 (CD183$^-$CD196$^+$) and Th1/Th17 (CD183$^+$CD196$^+$) were labeled with specific antibodies and quantified in the placebo (white bars) and *L. johnsonii* N6.2 (Ljo, darker bars) group at 0, 8 and 12 weeks of treatment. 11B) HLA-DR$^+$ and 11C) HLA-DR$^+$CD38$^+$ are shown for the Th1 and Th1/Th17 effector T cells. The concentration of cells shown has been normalized to the concentration found at T0 for each subject.
Figure 11B:
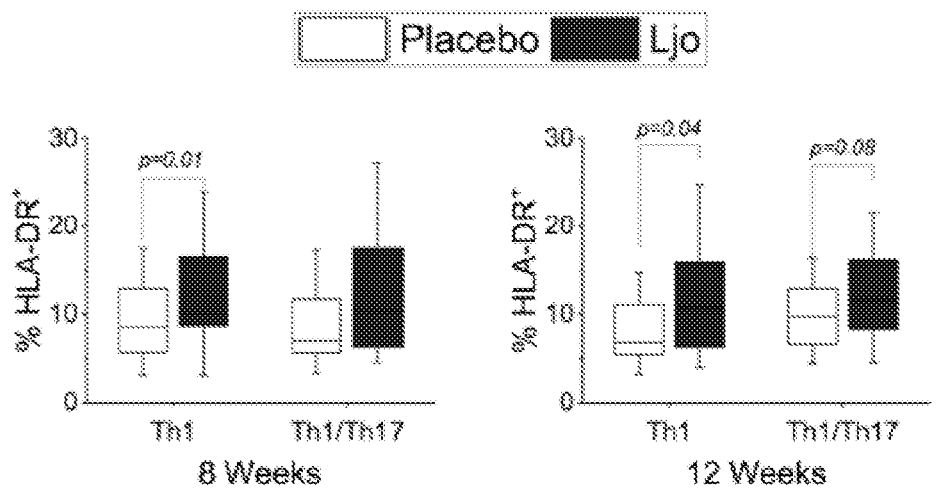
Figure 11C:
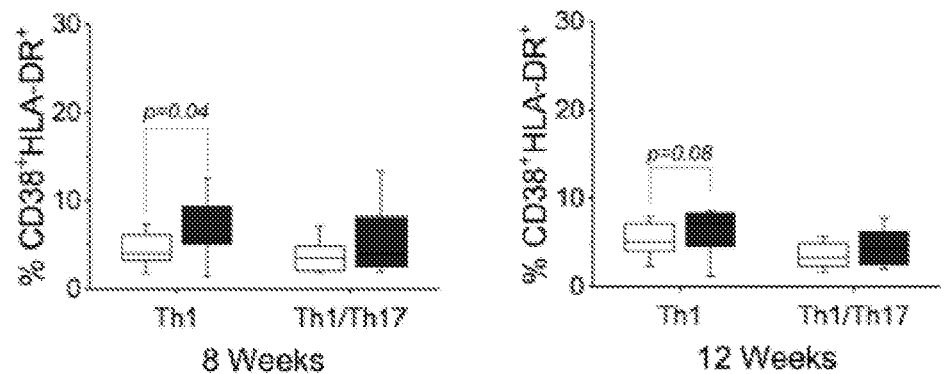

(iv) Differentiated Teff Subsets $CD4_+CD45RO^+$ T cells were separated into Th1 ($CD183^+CD196^-$), Th2 ($CD183^- CD196^-$), Th17 ($CD183^-CD196^+$) and Th1/Th17 ($CD183^+CD196^+$). CD38 and HLA-DR were included to indicate activation (FIG. 10). While significant differences were not observed among the total numbers for each of the Teff subsets (FIG. 11A), it was found that the number of activated Th1 ($HLA\text{-}DR^+$ and $HLA^-DR^+CD38^+$) were significantly increased (p<0.05) in the *L. johnsonii* treatment group (FIGS. 11B-11C). Interestingly, the numbers remained stable after 4 weeks of wash-out (p<0.05 and p<0.09, respectively). No significant differences were observed in the activation state of the Th2, Th17 or Th1/Th17 subsets during the treatment period; however, a trend toward increased Th17 ($HLA^-DR^+$) and Th1/Th17 ($HLA^-DR^+$) cells was observed after the wash-out period (p<0.1) (FIGS. 11A-11B).

(v) T Follicular Helper (TfH) Subsets $CD4^+CXCR5^+$ cells were separated into precursor ($CD45RA^-CD185^+CD279^+CD197^-$) and memory ($CD45RA^-CD185^+CD279^+CD183^-$) TfH cells (FIG. 10). Precursor TfH subset was significantly (p<0.05) decreased in the *L. johnsonii* N6.2 group after the wash-out period (12 weeks). Memory TfH was also decreased in the *L. johnsonii* N6.2 group but not statistically significant compared to placebo (Table 8).

(vi) Treg Subsets

CD4$^+$CD127$^{-/lo}$CD25$^+$ Tregs were separated into naïve (CD45RO$^-$) and memory (CD45RO$^+$). HLA$^-$DR and CD194 were also evaluated (FIG. 10). No differences were observed among the groups after 8 weeks of treatment; however, memory Tregs shoes a strong trend toward increased activation (HLA$^-$DR$^+$CD194$^+$) in the *L. johnsonii* N6.2 treatment group after the wash-out period (p=0.07) (Table 8).

Example 6—*L. Johnsonii* N6.2 Increased Circulating Levels of IgA

Figure 12:
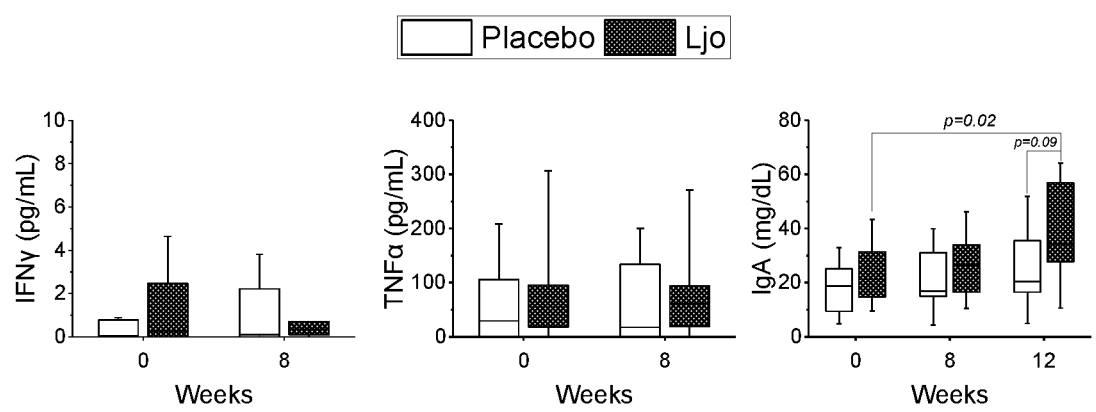
FIG. 12 shows determination of soluble markers. The concentrations of IFNγ, IgA, and TNFα were quantified in the placebo (white bars) and *L. johnsonii* N6.2 (Ljo, dark bars) group at time 0 and after 8 weeks of treatment or after the wash-out (12 weeks).

Based on the results obtained by immunophenotyping, we determined the levels of the following serum-soluble cytokines and immune markers: IL-6, TNF-α, IFN-γ, IFN-α, IL-2, soluble CD25 (IL-2Rα), and IgA by ELISA. IL-2 and IFN-α were below the detection limit and were not further analyzed. No statistical differences were obtained between the treatment groups or the time points for IL-6, TNF-α, IFN-γ, TNFα, soluble CD25 and CRP (p>0.1). A significant (p<0.05) increase in the concentration of IgA was observed during the wash-out period in the *L. johnsonii* treatment group while no differences observed in the placebo group (FIG. 12).

Example 7—*L. johnsonii* N6.2 Induces Minor Changes in the Microbiota of Healthy Subjects Based on the observations that many significant changes in the immune cell populations and IgA levels were observed 4 weeks after finalizing the probiotic treatment (wash-out period) we investigated whether *L. johnsonii* induced changes in the microbiota.

Figures 13A, 13B:
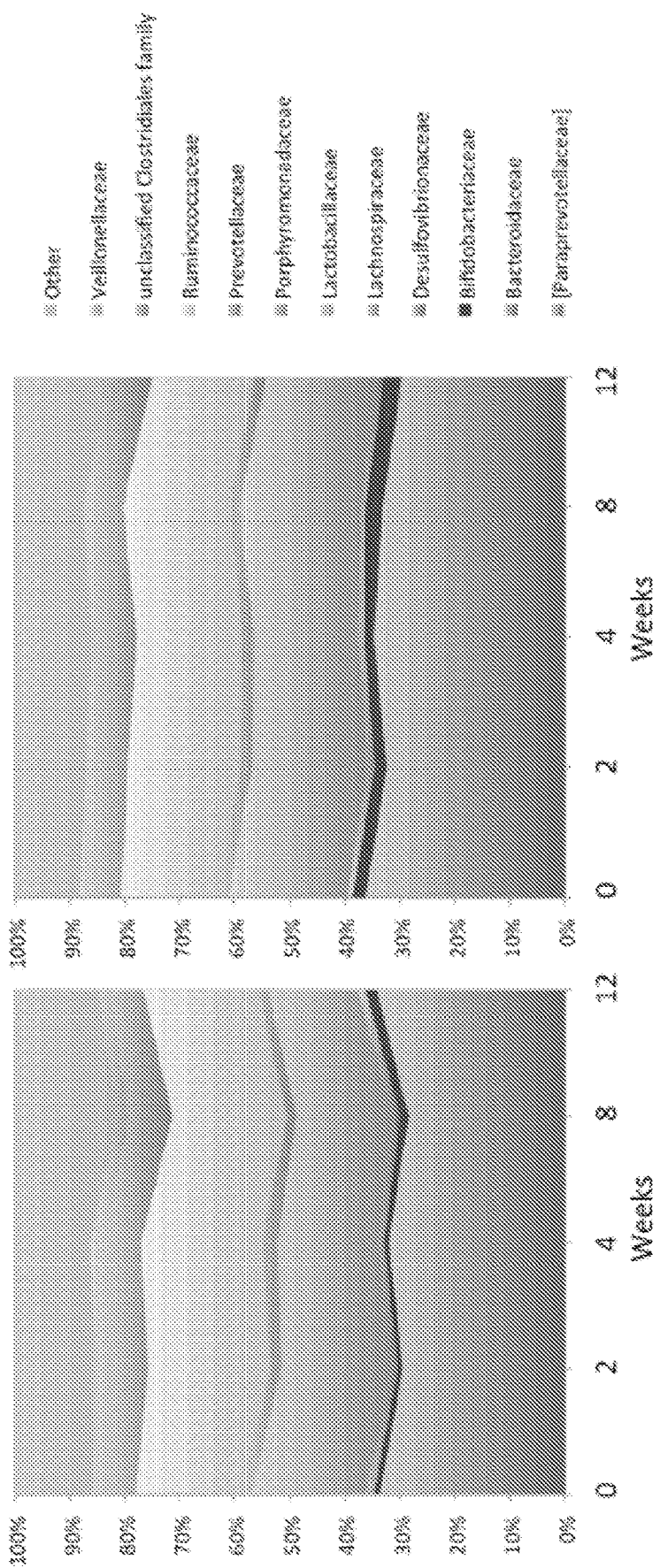
FIGS. 13A-13B show relative abundance of bacterial families in gut microbiota. The 10 most abundant families in stool samples from subjects given a 13A) placebo or 13B) *Lactobacillus johnsonii* N6.2 treatment. The Lactobacillaceae family was also included for comparison.
Figure 14:
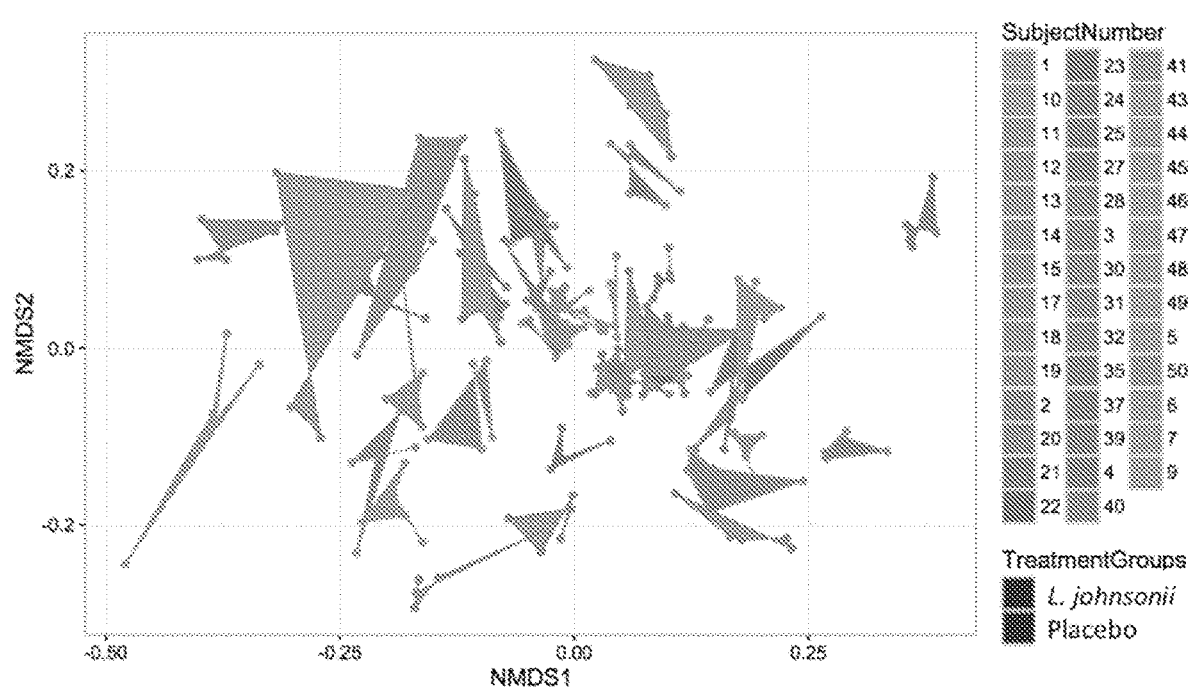
FIG. 14 shows a non-metric multidimensional scaling plot of microbial community similarity based on Bray-Curtis beta diversity of Illumina MiSeq 16S rRNA gene libraries. Points shown belong to the sampling time points: T0, T1=2 weeks, T2=4 weeks, T3=8 weeks (end of treatment), and T4=12 weeks. Polygons connect all the samples for one subject, and the bounding lines are colored according to the treatment group.

The microbiome was analyzed at time 0 and after 8 or 12 weeks of administration of the placebo or *L. johnsonii* N6.2. DNA was extracted from all stool samples, and the microbial communities were characterized by sequencing the V4 region of the 16S rDNA with Illumina MiSeq. An average of 54,743±15,800 sequencing reads per sample were obtained. Approximately 380,933 operational taxonomic units (OTUs) were detected, representing 173 families. The ten most abundant families detected were Bacteroidaceae, Lachnospiraceae, Ruminococcaceae, Prevotellaceae, Paraprevotellaceae, an unclassified Clostridiales family, Bifidobacteriaceae, Desulfovibrionaceae, Porphyromonadaceae, and Veillonellaceae (FIGS. 13A-13B), which was consistent throughout the time course of the study, although variation between individuals was observed. Bacterial communities clustered only by individual (ANOSIM R=0.921, p<0.01), and the community structure did not differ significantly by treatment (ANOSIM R=0.011, p=0.05) or over time (ANOSIM R=-0.017, p>0.99). In addition, community structure was not correlated with the combined effects of treatment and time (PERMANOVA R2=0.002, p=1.00) (FIG. 14). The statistical analysis showed that the relative abundance of genera or families was not significantly different between treatment groups or time points.

Due to the high variability observed in the microbiome among the subjects, we tested if the microbiome of each subject could be used to determine changes for each individual over time. Using this normalization approach, it was found that of the 173 families in the dataset, only 34 changed in relative abundance between weeks 0 and 8. The change per family was compared between the two treatment groups by Welch's two-sample t-test. Although no significant differences at p<0.05 were obtained, two families, Prevotellaceae and Ruminococcaceae showed trends with p<0.1 (Table 9) while families Lactobacillaceae, Erysipelotrichaceae and Odoribacteraceae showed values of p=0.17.

After the wash-out period, the observed microbial changes induced by *L. johnsonii* supplementation (i.e., increase in Ruminococcaceae, Lactobacillaceae, and Erysipelotrichaceae; or decrease in Prevotellaceae and Odoribacteraceae) were reverted such that the families returned to their initial abundancies. Interestingly, one family, Christensenellaceae significantly increased in concentration in the *L. johnsonii* treated group after 12 weeks (after the wash-out period) (p<0.05) while the Clostridiaceae and Bacteroidaceae families showed trends to increase or decrease, respectively (p=0.06 and p=0.09, respectively). However, when this normalization method was tested at the genus level no statistical differences were observed.

TABLE 1

Characteristics of the participants and compliance

|  | Placebo (n = 21) | Ljo[1] (n = 21) |
|---|---|---|
| Gender (M/F), n | 7/14 | 5/16 |
| Age, years Median (range) | 21 (18-48) | 23 (18-36) |
| Race/ethnicity, n (%) | | |
| Asian | 2 (10%) | 4 (19%) |
| African-American | 1 (5%) | 1 (5%) |
| Hispanic | 3 (14%) | 4 (19%) |
| White | 18 (86%) | 12 (57%) |
| Other | 0 | 3 (14%)[2] |
| BMI, mean (SD) | 23.6 ± 4.7 | 23.6 ± 4.2 |
| Blood pressure (mean mmHg) | 116/75 | 119/74 |
| Compliance (%) | | |
| Supplement protocol | 88.7 ± 10.0 | 92.9 ± 8.3 |
| Questionnaires protocol | 86.6 ± 14.4 | 90.7 ± 9.7 |

[1]*Lactobacillus johnsonii* N6.2
[2]Participants that classified themselves as other included n = 2 Hawaiian and n = 1 Unknown

TABLE 2

Summary of the results obtained for relevant indicators of kidney and liver function.

| Measure | Normal Values | Placebo (n = 20) Weeks | | | | |
|---|---|---|---|---|---|---|
|  |  | 0 | 2 | 4 | 8 | 12 |
| Glucose (mg/dL) | 70-100 | 80.0 ± 7.9 | 84.5 ± 1.5 | 84.6 ± 1.7 | 83.4 ± 1.7 | 83.2 ± 1.6 |
| KIDNEY FUNCTION | | | | | | |
| Urea (mg/dL) | 7-20 | 12.6 ± 4.9 | 13.8 ± 0.5 | 14.4 ± 0.7 | 13.7 ± 0.6 | 12.7 ± 0.6 |
| Creatinine (mg/dL) | 0.8-1.4 | 0.85 ± 0.28 | 0.81 ± 0.01 | 0.81 ± 0.02 | 0.77 ± 0.02 | 0.76 ± 0.01 |

TABLE 2-continued

Summary of the results obtained for relevant indicators of kidney and liver function.

LIVER FUNCTION

| | | | | | | |
|---|---|---|---|---|---|---|
| Aspartate Aminotransferase (IU/L) | 10-34 | 25.8 ± 7.2 | 23.2 ± 1.0 | 26.8 ± 1.5 | 25.1 ± 1.4 | 24.7 ± 1.4 |
| Alanine Aminotransferase (IU/L) | 8-37 | 19.9 ± 8.3 | 18.5 ± 1.2 | 22.3 ± 1.8 | 21.1 ± 2.1 | 18.9 ± 2.0 |
| Alkaline Phosphatase (IU/L) | 44-147 | 63.4 ± 14.6 | 66.9 ± 1.6 | 64.5 ± 1.9 | 71.1 ± 2.1 | 71.7 ± 2.0 |
| Total Bilirubin (mg/dL) | 0.2-1.9 | 0.53 ± 0.18 | 0.60 ± 0.05 | 0.63 ± 0.04 | 0.54 ± 0.05 | 0.58 ± 0.06 |

| | Normal | L. johnsonii N6.2 (n = 21) Weeks | | | | |
|---|---|---|---|---|---|---|
| Measure | Values | 0 | 2 | 4 | 8 | 12 |
| Glucose (mg/dL) | 70-100 | 80.9 ± 8.4 | 84.3 ± 1.5 | 84.6 ± 1.7 | 84.9 ± 1.7 | 85.3 ± 1.6 |

KIDNEY FUNCTION

| | | | | | | |
|---|---|---|---|---|---|---|
| Urea (mg/dL) | 7-20 | 12.8 ± 3.4 | 13.9 ± 0.5 | 15.1 ± 0.8 | 14.3 ± 0.6 | 13.8 ± 0.6 |
| Creatinine (mg/dL) | 0.8-1.4 | 0.79 ± 0.16 | 0.83 ± 0.01 | 0.81 ± 0.02 | 0.78 ± 0.02 | 0.76 ± 0.01 |

LIVER FUNCTION

| | | | | | | |
|---|---|---|---|---|---|---|
| Aspartate Aminotransferase (IU/L) | 10-34 | 25.2 ± 6.9 | 26.0 ± 1.0 | 24.1 ± 1.4 | 27.1 ± 1.4 | 25.7 ± 1.4 |
| Alanine Aminotransferase (IU/L) | 8-37 | 16.2 ± 5.6 | 19.7 ± 1.3 | 18.9 ± 1.7 | 20.8 ± 2.1 | 21.1 ± 2.0 |
| Alkaline Phosphatase (IU/L) | 44-147 | 69.1 ± 17.4 | 65.2 ± 1.6 | 69.0 ± 1.9 | 69.3 ± 2.1 | 68.6 ± 2.0 |
| Total Bilirubin (mg/dL) | 0.2-1.9 | 0.52 ± 0.12 | 0.65 ± 0.05 | 0.59 ± 0.04 | 0.70 ± 0.05 | 0.64 ± 0.06 |

TABLE 3

Gastrointestinal Symptom Rating Scale scores

| | Abdominal Pain[a] | | Reflux[b] | | Diarrhea[c] | | Indigestion[d] | | Constipation[e] | |
|---|---|---|---|---|---|---|---|---|---|---|
| Period | Placebo | Ljo | Placebo | Ljo | Placebo | Ljo | Placebo | Ljo | Placebo | Ljo |
| Baseline | 1.6 ± 0.1 | 1.3 ± 0.1 | 1.2 ± 0.1 | 1.1 ± 0.1 | 1.4 ± 0.2 | 1.3 ± 0.1 | 1.9 ± 0.1 | 1.4 ± 0.1* | 1.4 ± 0.1 | 1.3 ± 0.1 |
| Week 1 | 1.7 ± 0.1 | 1.2 ± 0.1* | 1.1 ± 0.1 | 1.0 ± 0.1 | 1.3 ± 0.1 | 1.4 ± 0.1 | 1.7 ± 0.1 | 1.4 ± 0.1* | 1.3 ± 0.1 | 1.1 ± 0.1 |
| Week 2 | 1.7 ± 0.1 | 1.1 ± 0.1*** | 1.2 ± 0.1 | 1.1 ± 0.1 | 1.5 ± 0.2 | 1.3 ± 0.2 | 1.8 ± 0.1 | 1.3 ± 0.1*** | 1.5 ± 0.2 | 1.2 ± 0.2 |
| Week 3 | 1.4 ± 0.1 | 1.1 ± 0.1* | 1.3 ± 0.1 | 1.1 ± 0.1 | 1.4 ± 0.1 | 1.3 ± 0.1 | 1.7 ± 0.1 | 1.3 ± 0.1* | 1.4 ± 0.1 | 1.2 ± 0.1 |
| Week 4 | 1.5 ± 0.1 | 1.1 ± 0.1* | 1.2 ± 0.1 | 1.1 ± 0.1 | 1.5 ± 0.2 | 1.4 ± 0/1 | 2.0 ± 0.1 | 1.3 ± 0.1** | 1.5 ± 0.2 | 1.2 ± 0.1 |
| Week 5 | 1.5 ± 0.1 | 1.1 ± 0.1** | 1.2 ± 0.1 | 1.0 ± 0.1 | 1.4 ± 0.1 | 1.2 ± 0.1 | 1.8 ± 0.2 | 1.3 ± 0.1* | 1.3 ± 0.1 | 1.2 ± 0.1 |
| Week 6 | 1.4 ± 0.1 | 1.1 ± 0.1* | 1.3 ± 0.2 | 1.2 ± 0.2 | 1.5 ± 0.2 | 1.2 ± 0.2 | 1.6 ± 0.1 | 1.3 ± 0.1* | 1.3 ± 0.1 | 1.2 ± 0.1 |
| Week 7 | 1.6 ± 0.1 | 1.0 ± 0.1** | 1.2 ± 0.1 | 1.0 ± 0.1* | 1.2 ± 0.1 | 1.1 ± 0.1 | 1.7 ± 0.1 | 1.2 ± 0.1** | 1.4 ± 0.1 | 1.1 ± 0.1* |
| Week 8 | 1.6 ± 0.1 | 1.1 ± 0.1** | 1.2 ± 0.1 | 1.0 ± 0.1 | 1.4 ± 0.1 | 1.1 ± 0.1 | 1.7 ± 0.1 | 1.2 ± 0.1** | 1.6 ± 0.1 | 1.1 ± 0.1* |
| Washout 1 | 1.5 ± 0.1 | 1.0 ± 0.1** | 1.2 ± 0.1 | 1.0 ± 0.1* | 1.5 ± 0.1 | 1.1 ± 0.1* | 1.8 ± 0.1 | 1.2 ± 0.1** | 1.4 ± 0.1 | 1.1 ± 0.1* |
| Washout 2 | 1.4 ± 0.1 | 1.0 ± 0.1*** | 1.1 ± 0.1 | 1.0 ± 0.1 | 1.3 ± 0.2 | 1.2 ± 0.2 | 1.7 ± 0.1 | 1.3 ± 0.1* | 1.5 ± 0.1 | 1.1 ± 0.1* |
| Washout 3 | 1.7 ± 0.1 | 1.1 ± 0.1*** | 1.3 ± 0.1 | 1.1 ± 0.1 | 1.4 ± 0.1 | 1.2 ± 0.1 | 1.9 ± 0.1 | 1.3 ± 0.1*** | 1.4 ± 0.1 | 1.1 ± 0.1* |
| Washout 4 | 1.5 ± 0.1 | 1.2 ± 0.1 | 1.3 ± 0.1 | 1.2 ± 0.1 | 1.4 ± 0.1 | 1.1 ± 0.1* | 1.8 ± 0.1 | 1.2 ± 0.1*** | 1.3 ± 0.1 | 1.1 ± 0.1 |

[a]Abdominal pain syndrome includes abdominal pain, hunger pains, and nausea symptoms.
[b]Reflux syndrome includes heartburn and acid regurgitation symptoms.
[c]Indigestion syndrome includes stomach rumbling, bloating, burping, and increased flatus symptoms.
[d]Constipation syndrome includes constipation, hard stools, and feeling of incomplete evacuation symptoms.
[e]Diarrhea syndrome includes diarrhea, loose stools, and urgent need for defecation symptoms.
Ljo correspond to *Lactobacillus johnsonii* N6.2
Data presented as Least Squares Mean ± SEM.
*p-value < 0.05;
**p-value < 0.01;
***p-value < 0.001

TABLE 4

Daily questionnaire syndrome scores

| | GI Distress[a] | | Epidermal[b] | | Cephalic[c] | |
|---|---|---|---|---|---|---|
| Period | Placebo | Ljo | Placebo | Ljo | Placebo | Ljo |
| Baseline | 3.1 ± 0.5 | 1.6 ± 0.5§ | 0.3 ± 0.2 | 0.1 ± 0.2 | 0.4 ± 0.1 | 0.5 ± 0.1 |
| Week 1 | 2.2 ± 0.3 | 1.1 ± 0.3* | 0.5 ± 0.2 | 0.01 ± 0.2 | 0.4 ± 0.1 | 0.4 ± 0.1 |
| Week 2 | 1.7 ± 0.3 | 1.1 ± 0.3 | 0.6 ± 0.2 | 0.01 ± 0.2* | 0.9 ± 0.2 | 0.2 ± 0.2** |
| Week 3 | 2.0 ± 0.4 | 0.8 ± 0.4* | 0.5 ± 0.2 | 0.07 ± 0.2 | 0.4 ± 0.1 | 0.3 ± 0.1 |
| Week 4 | 2.2 ± 0.3 | 1.0 ± 0.3** | 0.4 ± 0.2 | 0.07 ± 0.2 | 0.5 ± 0.1 | 0.05 ± 0.1** |
| Week 5 | 1.9 ± 0.3 | 1.1 ± 0.3* | 0.4 ± 0.2 | 0.03 ± 0.2 | 0.6 ± 0.1 | 0.2 ± 0.1* |
| Week 6 | 1.5 ± 0.2 | 0.9 ± 0.2 | 0.3 ± 0.2 | 0.02 ± 0.2 | 0.6 ± 0.1 | 0.02 ± 0.1** |
| Week 7 | 2.0 ± 0.2 | 0.8 ± 0.2** | 0.3 ± 0.1 | 0.01 ± 0.1 | 0.6 ± 0.1 | 0.04 ± 0.1*** |
| Week 8 | 1.6 ± 0.3 | 0.7 ± 0.3* | 0.4 ± 0.2 | 0.02 ± 0.2 | 0.3 ± 0.1 | 0.04 ± 0.1* |

TABLE 4-continued

Daily questionnaire syndrome scores

| Washout 1 | 2.1 ± 0.3 | 0.8 ± 0.3** | 0.2 ± 0.1 | 0.01 ± 0.1 | 0.3 ± 0.1 | 0.03 ± 0.1 |
|---|---|---|---|---|---|---|
| Washout 2 | 2.2 ± 0.4 | 0.7 ± 0.4** | 0.2 ± 0.1 | 0.01 ± 0.1* | 0.6 ± 0.1 | 0.04 ± 0.1*** |
| Washout 3 | 2.6 ± 0.5 | 1.0 ± 0.5* | 0.3 ± 0.1 | 0.07 ± 0.1* | 0.4 ± 0.1 | 0.1 ± 0.1 |
| Washout 4 | 1.9 ± 0.4 | 0.7 ± 0.4* | 0.3 ± 0.1 | 0.07 ± 0.1* | 0.4 ± 0.1 | 0.1 ± 0.1 |

| | Ear-Nose-Throat[d] | | Psychological[e] | | Emetic[f] | |
|---|---|---|---|---|---|---|
| Period | Placebo | Ljo | Placebo | Ljo | Placebo | Ljo |
| Baseline | 0.7 ± 0.2 | 0.6 ± 0.2 | 1.7 ± 0.6 | 2.6 ± 0.6 | 0.07 ± 0.06 | 0.13 ± 0.06 |
| Week 1 | 1.2 ± 0.4 | 0.7 ± 0.4 | 1.2 ± 0.5 | 2.0 ± 0.5 | 0.06 ± 0.03 | 0.02 ± 0.03 |
| Week 2 | 1.3 ± 0.3 | 0.4 ± 0.3* | 2.1 ± 0.6 | 1.4 ± 0.6 | 0.09 ± 0.06 | 0.01 ± 0.06 |
| Week 3 | 1.1 ± 0.4 | 0.8 ± 0.4 | 1.7 ± 0.4 | 0.9 ± 0.4 | 0.08 ± 0.07 | 0.13 ± 0.07 |
| Week 4 | 1.1 ± 0.3 | 0.3 ± 0.3* | 1.7 ± 0.6 | 1.6 ± 0.6 | 0.10 ± 0.05 | 0.01 ± 0.05 |
| Week 5 | 1.2 ± 0.3 | 0.4 ± 0.3 | 1.9 ± 0.5 | 1.2 ± 0.5 | 0.10 ± 0.05 | 0.02 ± 0.05 |
| Week 6 | 1.0 ± 0.3 | 0.3 ± 0.3 | 1.8 ± 0.5 | 1.0 ± 0.5 | 0.08 ± 0.03 | 0.02 ± 0.03* |
| Week 7 | 0.8 ± 0.2 | 0.2 ± 0.2* | 1.7 ± 0.5 | 1.0 ± 0.5 | 0.19 ± 0.07 | 0.01 ± 0.07 |
| Week 8 | 0.5 ± 0.2 | 0.1 ± 0.2 | 1.8 ± 0.4 | 0.8 ± 0.4 | 0.04 ± 0.03 | 0.02 ± 0.03 |
| Washout 1 | 0.8 ± 0.3 | 0.2 ± 0.3 | 1.8 ± 0.4 | 0.8 ± 0.4 | 0.06 ± 0.04 | 0.02 ±± 0.04 |
| Washout 2 | 0.6 ± 0.2 | 0.3 ± 0.2 | 1.6 ± 0.4 | 0.8 ± 0.4 | 0.11 ± 0.03 | 0.02 ± 0.03* |
| Washout 3 | 0.7 ± 0.2 | 0.4 ± 0.2 | 1.9 ± 0.4 | 1.1 ± 0.4 | 0.17 ± 0.06 | 0.06 ± 0.06 |
| Washout 4 | 1.0 ± 0.3 | 0.4 ± 0.3 | 2.1 ± 0.5 | 1.0 ± 0.5 | 0.08 ± 0.05 | 0.08 ± 0.05 |

[a]Gastrointestinal distress syndrome includes daily symptoms of bloating, flatulence, stomach noises, abdominal cramps.
[b]Epidermal syndrome includes daily symptoms of itching, skin rash, skin redness/flushing.
[c]Cephalic syndrome includes daily symptoms of headache and dizziness.
[d]Ear-Nose-Throat syndrome includes daily symptoms of sore throat, runny eyes, nasal congestion, and blocked ear canal.
[e]Psychological syndrome includes daily symptoms of anxiety, depression and stress.
[f]Emetic syndrome includes daily symptoms of nausea and vomiting.
Ljo correspond to *Lactobacillus johnsonii* N6.2
Data presented as Least Squares mean ± SEM.
*p < 0.05;
**p < 0.01;
***p < 0.001.

TABLE 5

Select individual symptoms of the daily and weekly questionnaires.

| | Stomachache or pain[w] | | Bloating[d] | | Cramping[d] | | Abdominal Noises[d] |
|---|---|---|---|---|---|---|---|
| Period | Placebo | Ljo | Placebo | Ljo | Placebo | Ljo | Placebo |
| Baseline | 1.7 ± 0.1 | 1.0 ± 0.1 | 0.4 ± 0.05 | 0.1 ± 0.05 | 0.3 ± 0.05 | 0.01 ± 0.05 | 0.3 ± 0.05 |
| Week 1 | 1.9 ± 0.2 | 1.2 ± 0.2* | 0.4 ± 0.1 | 0.2 ± 0.1 | 0.4 ± 0.1 | 0.1 ± 0.1** | 0.3 ± 0.1 |
| Week 2 | 2.3 ± 0.2 | 1.0 ± 0.2*** | 0.3 ± 0.1 | 0.2 ± 0.1 | 0.4 ± 0.1 | 0.01 ± 0.1** | 0.3 ± 0.1 |
| Week 3 | 1.5 ± 0.2 | 1.1 ± 0.2* | 0.3 ± 0.1 | 0.05 ± 0.1** | 0.4 ± 0.1 | 0.01 ± 0.1** | 0.4 ± 0.1 |
| Week 4 | 1.5 ± 0.1 | 1.0 ± 0.1** | 0.6 ± 0.1 | 0.1 ± 0.1** | 0.2 ± 0.1 | 0.01 ± 0.1** | 0.3 ± 0.1 |
| Week 5 | 1.4 ± 0.1 | 0.9 ± 0.1* | 0.4 ± 0.1 | 0.04 ± 0.1** | 0.1 ± 0.1 | 0.04 ± 0.1 | 0.3 ± 0.1 |
| Week 6 | 1.4 ± 0.1 | 1.0 ± 0.1* | 0.2 ± 0.1 | 0.2 ± 0.1 | 0.2 ± 0.05 | 0.01 ± 0.05* | 0.2 ± 0.1 |
| Week 7 | 1.8 ± 0.2 | 0.9 ± 0.2*** | 0.3 ± 0.1 | 0.1 ± 0.1 | 0.3 ± 0.1 | 0.01 ± 0.1** | 0.3 ± 0.1 |
| Week 8 | 1.8 ± 0.2 | 1.0 ± 0.2** | 0.3 ± 0.2 | 0.05 ± 0.1* | 0.2 ± 0.1 | 0.01 ± 0.2** | 0.3 ± 0.1 |
| Washout 1 | 1.6 ± 0.2 | 1.0 ± 0.2* | 0.5 ± 0.1 | 0.3 ± 0.2* | 0.2 ± 0.1 | 0.01 ± 0.1** | 0.2 ± 0.1 |
| Washout 2 | 1.5 ± 0.2 | 1.0 ± 0.2 | 0.6 ± 0.1 | 0.1 ± 0.1** | 0.3 ± 0.1 | 0.01 ± 0.1* | 0.3 ± 0.1 |
| Washout 3 | 1.9 ± 0.2 | 1.0 ± 0.2** | 0.6 ± 0.1 | 0.1 ± 0.1** | 0.5 ± 0.2 | 0.01 ± 0.2 | 0.4 ± 0.2 |
| Washout 4 | 1.6 ± 0.1 | 1.0 ± 0.1* | 0.5 ± 0.1 | 0.02 ± 0.1** | 0.2 ± 0.1 | 0.01 ± 0.1* | 0.3 ± 0.1 |

| | Abdominal Noises[d] | Headache[d] | | Anxiety[d] | |
|---|---|---|---|---|---|
| Period | Ljo | Placebo | Ljo | Placebo | Ljo |
| Baseline | 0.06 ± 0.05 | 0.4 ± 0.04 | 0.1 ± 0.04 | 0.5 ± 0.1 | 0.3 ± 0.1 |
| Week 1 | 0.1 ± 0.1 | 0.3 ± 0.1 | 0.4 ± 0.1 | 0.3 ± 0.2 | 0.6 ± 0.2 |
| Week 2 | 0.1 ± 0.1 | 0.7 ± 0.1 | 0.2 ± 0.1** | 0.5 ± 0.2 | 0.3 ± 0.2 |
| Week 3 | 0.04 ± 0.1* | 0.3 ± 0.1 | 0.2 ± 0.1 | 0.4 ± 0.1 | 0.2 ± 0.1 |
| Week 4 | 0.1 ± 0.1* | 0.4 ± 0.1 | 0.04 ± 0.1** | 0.4 ± 0.2 | 0.4 ± 0.2 |
| Week 5 | 0.1 ± 0.1* | 0.4 ± 0.1 | 0.2 ± 0.1 | 0.4 ± 0.1 | 0.3 ± 0.1 |
| Week 6 | 0.02 ± 0.1 | 0.5 ± 0.1 | 0.02 ± 0.1** | 0.5 ± 0.2 | 0.2 ± 0.2 |
| Week 7 | 0.01 ± 0.1** | 0.4 ± 0.1 | 0.01 ± 0.1*** | 0.5 ± 0.2 | 0.2 ± 0.2 |
| Week 8 | 0.01 ± 0.1** | 0.2 ± 0.05 | 0.02 ± 0.1** | 0.5 ± 0.2 | 0.2 ± 0.2 |

TABLE 5-continued

Select individual symptoms of the daily and weekly questionnaires.

|  |  |  |  |  |  |
|---|---|---|---|---|---|
| Washout 1 | 0.01 ± 0.1** | 0.2 ± 0.1 | 0.03 ± 0.1 | 0.5 ± 0.1 | 0.1 ± 0.1* |
| Washout 2 | 0.01 ± 0.1* | 0.4 ± 0.1 | 0.01 ± 0.1*** | 0.5 ± 0.1 | 0.1 ± 0.1* |
| Washout 3 | 0.04 ± 0.2 | 0.3 ± 0.2 | 0.1 ± 0.2 | 0.5 ± 0.2 | 0.1 ± 0.1 |
| Washout 4 | 0.01 ± 0.1* | 0.3 ± 0.1 | 0.1 ± 0.1 | 0.6 ± 0.2 | 0.2 ± 0.1* |

Ljo correspond to *Lactobacillus johnsonii* N6.2.
Data presented as Least Squares mean ± SEM.
*p < 0.05;
**p < 0.01;
***p < 0.001.
$^w$ = from weekly questionnaire;
$^d$ = from daily questionnaire.

TABLE 6

Summary of the concentrations of metabolites obtained within the tryptophan pathway.

| Metabolite[1] | Weeks | | | | |
|---|---|---|---|---|---|
| (nMol) | 0 | 2 | 4 | 8 | 12 |
| Placebo (n = 20) | | | | | |
| Serotonine | 0.024 ± 0.022 | 0.026 ± 0.013 | 0.026 ± 0.009 | 0.041 ± 0.015 | 0.049 ± 0.014 |
| Kynurenine | 1.90 ± 0.40 | 2.00 ± 0.10 | 2.00 ± 0.08 | 2.01 ± 0.08 | 1.97 ± 0.14 |
| Tryptophan | 61.2 ± 8.2 | 63.3 ± 2.4 | 65.2 ± 3.0 | 63.9 ± 2.5 | 60.3 ± 5.7 |
| Xanthurenic acid | 0.015 ± 0.006 | 0.018 ± 0.002 | 0.018 ± 0.002 | 0.017 ± 0.002 | 0.014 ± 0.003 |
| Kynurenic acid | 0.079 ± 0.04 | 0.110 ± 0.010 | 0.103 ± 0.009 | 0.106 ± 0.011 | 0.092 ± 0.010 |
| K:T (×1000)[2] | 31.5 ± 5.4 | 32.6 ± 1.2 | 31.3 ± 1.2 | 32.3 ± 1.1 | 33.3 ± 2.2 |
| *L. johnsonii* N6.2 (n = 21) | | | | | |
| Serotonine | 0.022 ± 0.016 | 0.036 ± 0.013 | 0.021 ± 0.009 | 0.036 ± 0.014 | 0.022 ± 0.015 |
| Kynurenine | 2.0 ± 0.4 | 2.1 ± 0.1 | 2.12 ± 0.09 | 2.14 ± 0.08 | 2.30 ± 0.15 |
| Tryptophan | 61.0 ± 10.8 | 66.0 ± 2.5 | 68.7 ± 3.2 | 67.1 ± 2.5 | 70.6 ± 6.1 |
| Xanthurenic acid | 0.017 ± 0.008 | 0.019 ± 0.002 | 0.020 ± 0.002 | 0.020 ± 0.002 | 0.020 ± 0.003 |
| Kynurenic acid | 0.097 ± 0.005 | 0.114 ± 0.010 | 0.109 ± 0.009 | 0.128 ± 0.011 | 0.116 ± 0.010 |
| K:T (×1000)[2] | 33.3 ± 6.6 | 32.3 ± 1.2 | 31.9 ± 1.2 | 32.1 ± 1.1 | 34.1 ± 2.4 |

[1] Anthranilic acid was also determined however the values obtained were below the detection limit of the instrument (3 ng/mL).
[2] Ratio kynurenine: tryptophan

TABLE 7

B cells, Monocytes, Dendritic cells and Natural Killer subset.

| Lymphocytes | Subpopulations | 8 weeks | | 12 weeks | |
|---|---|---|---|---|---|
| | | Placebo | Ljo | Placebo | Ljo |
| B cells % (CD3$^-$CD19$^+$) | | 10.7 ± 0.4 | 10.9 ± 0.4 | 11.8 ± 0.4 | 11.3 ± 0.4 |
| | Transitional % (CD27$^-$IgD$^+$CD24$^{hi}$CD38$^{hi}$) | 3. ± 0.3 | 3.2 ± 0.3 | 2.8 ± 0.3 | 3.5 ± 0.3 |
| | Naive % (CD27$^-$IgD$^+$CD24$^{lo/-}$CD38$^{lo/-}$) | 67.3 ± 1.3 | 68.3 ± 1.3 | 65.8 ± 1.1 | 67.4 ± 1.1 |
| | Non-class-switched Memory % (CD20$^{hi}$CD27$^+$IgD$^+$) | 8.7 ± 1.0 | 7.1 ± 1.0 | 10.7 ± 1.0 | 8.4 ± 1.0$^\Psi$ |
| | Class-switched Memory % (CD20$^{hi}$CD27$^+$IgD$^-$) | 20.3 ± 1.1 | 21.4 ± 1.1 | 20.2 ± 0.8 | 20.7 ± 0.9 |
| | Plasmablast (CD20$^{lo/-}$CD38$^+$) | 0.56 ± 0.10 | 0.36 ± 0.10 | 0.36 ± 0.08 | 0.41 ± 0.08 |
| Granulocytes % | | 47.1 ± 1.7 | 47.8 ± 1.7 | 50.6 ± 1.8 | 51.8 ± 1.8 |
| MNC % (non-granulocytes) (CD3$^-$CD19$^-$CD20$^-$) | | 45.90 ± 2.1 | 48.8 ± 2.1 | 43.9 ± 1.8 | 41.5 ± 1.8 |
| | DC % (of MNC) (HLA-DR$^+$CD14$^-$CD16$^-$) | 0.89 ± 0.18 | 1.01 ± 0.17 | 1.04 ± 0.32 | 1.05 ± 0.31 |
| | HLA-DR mfi | 10966 ± 598 | 11068 ± 606 | 12369 ± 605 | 12335 ± 612 |
| | Myeloid % (CD11c$^+$CD123$^-$) | 63.2 ± 1.8 | 64.8 ± 1.8 | 66.0 ± 1.7 | 65.6 ± 1.7 |
| | Plasmacytoid % (CD123$^+$) | 22.5 ± 1.8 | 21.9 ± 1.8 | 22.5 ± 1.3 | 23.0 ± 1.3 |
| | Monocytes % (HLA-DR$^+$CD14$^+$ CD56$^-$) | 16.5 ± 0.9 | 17.1 ± 0.9 | 16.1 ± 1.1 | 19.7 ± 1.1* |

TABLE 7-continued

B cells, Monocytes, Dendritic cells and Natural Killer subset.

| Lymphocytes | Subpopulations | 8 weeks Placebo | 8 weeks Ljo | 12 weeks Placebo | 12 weeks Ljo |
|---|---|---|---|---|---|
| | HLA-DR mfi | 6423 ± 305 | 5855 ± 308 | 6015 ± 369 | 6209 ± 368 |
| | Classical % (CD16$^-$) | 88.3 ± 1.0 | 88.4 ± 1.0 | 90.5 ± 0.7 | 89.2 ± 0.7 |
| | Non-Classical % (CD16$^+$) | 11.6 ± 1.0 | 11.6 ± 1.0 | 9.5 ± 0.7 | 10.8 ± 0.7 |
| NK % (of lymphocytes) (CD3$^-$CD19$^-$CD14$^-$) | | 9.2 ± 0.7 | 10.6 ± 0.7 | 8.4 ± 0.7 | 10.4 ± 0.8$^\Psi$ |
| | CD16$^-$CD56$^{hi}$ % | 6.3 ± 0.7 | 5.7 ± 0.7 | 5.7 ± 0.6 | 5.7 ± 0.6 |
| | CD16$^+$CD56$^{lo/-}$ % | 84.8 ± 1.0 | 85.9 ± 1.0 | 84.9 ± 1.0 | 84.8 ± 1.0 |
| | CD16$^+$CD56$^{hi}$ % | 2.8 ± 0.4 | 2.2 ± 0.4 | 3.0 ± 0.2 | 2.5 ± 0.2 |

B cells (transitional, memory and plasmablast), Mononuclear cells (DC, Myeloid, Plasmacytoid and monocytes) and NKs were analyzed by multicolor flow cytometry using specific antibodies for CD3, CD11c, CD14, CD16, CD19, CD20, CD24, CD27, CD38, CD56 and CD123. The populations were analyzed after 8 and 12 week of consumption of the placebo or *L. johnsonii* N6.2 (Ljo).
Data presented as Least Squares mean ± SEM.
$^\Psi$p < 0.1;
*p < 0.05;
**p < 0.01.

TABLE 8

T cells subset: CD4$^+$ and CD8$^+$, Follicular helper, Regulatory and Conventional T cells were defined.

| Lymphocytes | Subpopulations | | 8 weeks Placebo | 8 weeks Ljo | 12 weeks Placebo | 12 weeks Ljo |
|---|---|---|---|---|---|---|
| T cells % (CD3$^+$) | | | 72.4 ± 0.9 | 71.7 ± 0.9 | 68.8 ± 1.2 | 69.0 ± 1.3 |
| CD4$^+$ T cells (CD3$^+$CD4$^+$) | | | 58.4 ± 0.6 | 56.6 ± 0.6* | 58.2 ± 0.6 | 57.5 ± 0.6 |
| | CD38$^-$HLA-DR$^-$ | | 35.5 ± 0.7 | 36.9 ± 0.8 | 35.2 ± 0.8 | 36.5 ± 0.8 |
| | CD38$^-$HLA-DR$^+$ | | 3.5 ± 0.2 | 3.8 ± 0.2 | 3.3 ± 0.2 | 3.5 ± 0.2 |
| | CD38$^+$HLA-DR$^-$ | | 58.1 ± 0.9 | 56.3 ± 1.0 | 58.7 ± 1.1 | 57.0 ± 1.1 |
| | CD38$^+$HLA-DR$^+$ | | 2.9 ± 0.2 | 3.1 ± 0.2 | 2.8 ± 0.2 | 3.0 ± 0.2 |
| | Naïve % (CD197$^+$CD45RA$^+$) | | 53.8 ± 0.9 | 52.6 ± 0.9 | 53.0 ± 1.1 | 52.2 ± 1.1 |
| | | CD279$^+$ mfi | 102.1 ± 6.5 | 93.7 ± 10.0 | 140.2 ± 10.0 | 123.7 ± 10.0 |
| | Tem % (CD197$^-$CD45RA$^-$) | | 9.9 ± 0.4 | 10.6 ± 0.4 | 10.3 ± 0.6 | 11.3 ± 0.6 |
| | | CD279$^+$ mfi | 148.2 ± 6.0 | 137.6 ± 5.9 | 201.0 ± 10.1 | 178.7 ± 10.1 |
| | Tcm % (CD197$^+$CD45RA$^-$) | | 35.8 ± 0.8 | 35.8 ± 0.8 | 36.4 ± 0.9 | 35.6 ± 0.9 |
| | | CD279$^+$ mfi | 108.3 ± 5.9 | 92.0 ± 5.9* | 158.5 ± 10.8 | 130.7 ± 10.7$^\Psi$ |
| | Temra % (CD197$^-$CD45RA$^+$) | | 0.40 ± 0.09 | 0.28 ± 0.08 | 0.32 ± 0.07 | 0.25 ± 0.07 |
| | | CD279 mfi | 134.3 ± 8.9 | 138.9 ± 8.8 | 186.9 ± 10.5 | 167.3 ± 10.5 |
| CD8$^+$ T cells (CD3$^+$CD8$^+$) | | | 32.2 ± 0.5 | 32.7 ± 0.5 | 32.5 ± 0.4 | 32.6 ± 0.4 |
| | CD38$^-$HLA-DR$^-$ | | 45.7 ± 1.4 | 46.2 ± 1.4 | 41.5 ± 1.4 | 44.7 ± 1.6 |
| | CD38$^-$HLA-DR$^+$ | | 7.6 ± 0.6 | 7.9 ± 0.6 | 7.1 ± 0.4 | 7.8 ± 0.4 |
| | CD38$^+$HLA-DR$^-$ | | 38.7 ± 1.3 | 35.7 ± 1.3 | 41.5 ± 1.2 | 36.9 ± 1.2** |
| | CD38$^+$HLA-DR$^+$ | | 8.3 ± 0.5 | 10.0 ± 0.6* | 8.9 ± 0.7 | 10.5 ± 0.7$^\Psi$ |
| | Naïve % (CD197$^+$CD45RA$^+$) | | 45.9 ± 1.2 | 41.4 ± 1.2** | 47.4 ± 1.5 | 43.9 ± 1.5$^\Psi$ |
| | | CD279 mfi | 112.8 ± 7.0 | 114.7 ± 7.0 | 115.6 ± 6.3 | 123.3 ± 6.5 |
| | Tem % (CD197$^-$CD45RA$^-$) | | 26.2 ± 1.6 | 31.8 ± 1.7* | 27.0 ± 1.6 | 30.0 ± 1.7 |
| | | CD279 mfi | 134.2 ± 6.7 | 115.9 ± 6.9* | 196.6 ± 14.2 | 162.4 ± 14.0$^\Psi$ |
| | Tcm % (CD197$^+$CD45RA$^-$) | | 11.3 ± 1.0 | 10.4 ± 1.0 | 12.4 ± 1.2 | 11.0 ± 1.2 |
| | | CD279 mfi | 116.4 ± 5.1 | 102.4 ± 5.2* | 160.2 ± 8.4 | 142.3 ± 8.4 |
| | Temra % (CD197$^-$CD45RA$^+$) | | 15.1 ± 1.1 | 16.0 ± 1.1 | 13.5 ± 0.9 | 14.8 ± 0.9 |
| | | CD279 mfi | 158.7 ± 10.7 | 180.8 ± 10.7 | 181.2 ± 12.2 | 204.7 ± 12.3 |
| T follicular helper (Tfh) CD4$^+$ | | | | | | |
| | Precursor % (CD45RA$^-$CD185$^+$CD279$^+$CD197$^-$) | | 0.25 ± 0.02 | 0.22 ± 0.02 | 0.89 ± 0.21 | 0.24 ± 0.21* |
| | Memory % (CD45RA$^-$CD185$^+$CD279$^+$CD183$^-$) | | 0.44 ± 0.04 | 0.43 ± 0.04 | 0.83 ± 0.12 | 0.58 ± 0.12 |
| Regulatory T cells (CD3$^+$CD4$^+$) | | | | | | |
| Treg % (CD25$^+$CD127$^{lo/-}$) | | | 5.7 ± 0.1 | 5.7 ± 0.1 | 5.3 ± 0.3 | 5.0 ± 0.3 |
| | Naïve % (CD45RO$^-$) | CD25 mfi | 411.6 ± 5.8 | 409.9 ± 6.0 | 372.3 ± 15.2 | 378.2 ± 15.0 |
| | Memory (CD45RO$^+$) | CD25 mfi | 585.4 ± 8.6 | 581.4 ± 8.8 | 546.1 ± 24.3 | 558.6 ± 23.9 |

TABLE 8-continued

T cells subset: CD4+ and CD8+, Follicular helper, Regulatory and Conventional T cells were defined.

| Lymphocytes | | Subpopulations | 8 weeks | | 12 weeks | |
|---|---|---|---|---|---|---|
| | | | Placebo | Ljo | Placebo | Ljo |
| T conventional % | CD45RO− | CD25 mfi | 14.4 ± 0.8 | 12.2 ± 0.8* | 13.7 ± 0.6 | 14.4 ± 0.7 |
| (CD25$^{lo/−}$CD127$^{hi}$CD194+) | CD45RO+ | CD25 mfi | 54.0 ± 2.0 | 52.6 ± 2.1 | 57.4 ± 3.4 | 54.8 ± 3.4 |

Data presented as Least Squares mean ± SEM.
$^{\Psi}p < 0.1$;
$^{*}p < 0.05$;
$^{**}p < 0.01$.

TABLE 9

Summary of the families that changed in abundance after 8 or 12 weeks of treatment[1]

| Family name | Change in Relative abundance (T8 − T0)[1] | | Change in Relative abundance (T12 − T0)[1] | | Change in Relative abundance (T12 − T8)[1] | |
|---|---|---|---|---|---|---|
| | Placebo | Ljo | Placebo | Ljo | Placebo | Ljo |
| Lachnospiraceae | 0.0030 | 0.0228 | −0.0070 | −0.0009 | −0.0100 | −0.0238 |
| Ruminococcaceae | −0.0060 | 0.0228* | 0.0051 | 0.0223 | 0.0075 | −0.0005 |
| Rikenellaceae | 0.0045 | 0.0024 | 0.0010 | 0.0019 | −0.0035 | −0.0005 |
| Porphyromonadaceae | 0.0065 | −0.0005 | 0.0020 | −0.0023 | −0.0045 | −0.00190 |
| Prevotellaceae | 0.0205 | −0.0152* | 0.0050 | −0.0071 | −0.0155 | 0.0081 |
| unclassified_Mollicutes | 0.0010 | 0.0024 | | | 0 | −0.0009 |
| unclassified_Clostridiales | 0.0015 | 0.0007 | 0.0040 | −0.0014 | 0.0005 | −0.0014 |
| Streptococcaceae | 0.0010 | 0.0014 | | | −0.0005 | −0.0019 |
| unclassified_Clostridiales2 | 0.0030 | −0.0014 | 0.0005 | 0.0014 | 0.0001 | 0 |
| Enterobacteriaceae | 0.0005 | 0.0009 | | | −0.0015 | 0.0024 |
| Desulfovibrionaceae | 0.0001 | 0 | | | −0.0030 | 0.0033 |
| Halomonadaceae | 0.0010 | 0 | | | −0.0015 | 0.0005** |
| Elusimicrobiaceae | 0 | 0.0009 | 0 | 0.0005 | 0 | −0.0005 |
| Veillonellaceae | −0.0025 | 0.0028 | −0.0010 | 0.0009 | 0.0015 | −0.0019 |
| Clostridiaceae | −0.0005 | 0.0009 | −0.0020 | 0.0067* | −0.0015 | 0.0057* |
| Verrucomicrobiaceae | 0.0020 | −0.0014 | | | 0.0120 | 0.0147 |
| unclassified_Cyanobacteria | 0 | 0 | 0 | 0 | 0 | 0 |
| Mogibacteriaceae | 0 | 0.0005 | 0 | 0 | 0 | −0.0005 |
| unclassified_Alphaproteobacteria | 0 | 0.0005 | 0 | 0 | 0.0010 | −0.0005 |
| Lactobacillaceae | −0.0010 | 0.0009 | 0.0005 | 0.0005 | 0.0015 | −0.0005 |
| Barnesiellaceae | −0.0005 | 0.0005 | −0.0005 | 0.0028 | 0 | 0.0024 |
| Erysipelotrichaceae | −0.0040 | 0.0033 | 0 | 0 | 0.0005 | −0.0009 |
| Christensenellaceae | 0 | 0 | −0.002 | 0.0033** | −0.0015 | 0.0033* |
| Odoribacteraceae | 0.0005 | −0.0014 | 0 | −0.0019 | −0.0005 | −0.0005 |
| Paraprevotellaceae | 0 | −0.0014 | −0.0005 | 0.0009 | −0.0005 | 0.0024 |
| Comamonadaceae | −0.0015 | 0 | | | 0.0010 | −0.0005 |
| Pasteurellaceae | −0.0010 | −0.0009 | | | 0.0020 | 0.0005 |
| unclassified_Streptophyta | 0 | −0.0024 | | | | |
| Alcaligenaceae | −0.0040 | −0.0024 | | | −0.0005 | −0.0029 |
| unclassified_Bacteroidales | −0.0015 | −0.0057 | | | | |
| Bifidobacteriaceae | −0.0075 | −0.0024 | −0.0055 | 0.0033 | 0.0020 | 0.0057 |
| Methanobacteriaceae | 0.4840 | −0.0033 | −0.0040 | −0.0019 | 0.0035 | 0.0014 |
| Bacteroidaceae | −0.0045 | −0.0305 | −0.0040 | −0.0450 | 0.0005 | −0.0147 |
| Coriobacteriaceae | | | 0.0010 | 0.0019 | 0.0040 | −0.0009 |
| Turicibacteraceae | | | 0 | 0 | 0 | 0 |
| Peptococcaceae | | | 0.0005 | 0.0005 | 0.0005 | 0.0005 |
| Bacteroidales family S24-7 | | | 0.0010 | −0.0071 | 0.0025 | −0.0014 |

Data presented as Least Squares mean ± SEM.
$^{*}p < 0.1$;
$^{**}p < 0.05$;
$^{***}p < 0.01$.
[1]Relative change in abundance was calculated as the difference between the mean in abundance at week 8 or 12 and the abundance at week 0.

We claim:

1. A method for alleviating symptoms of indigestion or abdominal pain in a human subject, comprising administering to the subject a composition comprising an effective amount of *Lactobacillus johnsonii* N6.2, wherein the effective amount is such to increase tryptophan levels and/or decrease kynurenine:tryptophan (K:T) ratio in the subject, wherein the effective amount administered comprises a daily dose of at least about $10^8$ CFU of *Lactobacillus johnsonii* N6.2; and wherein administering occurs for 8 weeks or more.

2. The method of claim 1, wherein the subject has not been diagnosed with type 1 diabetes.

3. The method of claim 1, comprising orally administering the composition to the subject.

4. The method of claim 1, wherein the composition is a food.

5. The method of claim 4, wherein the food is a fermented food.

6. The method of claim 1, wherein the composition is a dried powder.

7. The method of claim 6, wherein the dried powder is encapsulated in a capsule.

8. The method of claim 7, wherein the capsule is acid resistant.

9. The method of claim 8, wherein the capsule contains about $10^8$ CFU of *Lactobacillus johnsonii* N6.2.

10. The method of claim 1, wherein said administering increases circulating levels of Immunoglobulin A (IgA) in the subject.

11. A method for alleviating headaches in a subject, comprising administering to the subject a composition comprising an effective amount of *Lactobacillus johnsonii* N6.2, wherein the effective amount administered is a dose that comprises at least about $10^8$ CFU of *Lactobacillus johnsonii* N6.2; and wherein the subject has not be diagnosed with type-1 diabetes.

\* \* \* \* \*